(12) United States Patent
Kim et al.

(10) Patent No.: US 11,896,397 B2
(45) Date of Patent: Feb. 13, 2024

(54) DISPLAY DEVICE

(71) Applicant: SAMSUNG DISPLAY CO., LTD., Yongin-si (KR)

(72) Inventors: Chul Kim, Yongin-si (KR); Kang Bin Jo, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 0 days.

(21) Appl. No.: 18/152,640

(22) Filed: Jan. 10, 2023

(65) Prior Publication Data
US 2023/0397885 A1 Dec. 14, 2023

(30) Foreign Application Priority Data
Jun. 10, 2022 (KR) .................. 10-2022-0070505

(51) Int. Cl.
*A61B 5/00* (2006.01)
*A61B 5/021* (2006.01)
(Continued)

(52) U.S. Cl.
CPC ........ *A61B 5/6898* (2013.01); *A61B 5/02108* (2013.01); *A61B 5/02416* (2013.01); *G06F 3/0414* (2013.01); *G06F 3/0416* (2013.01); *G09G 3/3233* (2013.01); *G06F 3/0412* (2013.01); *G06F 3/0446* (2019.05);
(Continued)

(58) Field of Classification Search
CPC .... G06F 3/0412; G06F 3/0414; G06F 3/0416; G06F 3/0446; G09G 3/2007; G09G 3/3233; G09G 2300/0819; G09G 2300/0842; G09G 2310/0213; G09G 2310/08; G09G 2354/00; G09G 2360/14; G09G 2380/08; A61B 5/02108; A61B 5/02416; A61B 5/6898
See application file for complete search history.

(56) References Cited

U.S. PATENT DOCUMENTS

2003/0234759 A1* 12/2003 Bergquist ................. G09G 3/20
    345/92
2011/0148835 A1* 6/2011 Yamazaki ............ G09G 3/2003
    345/207
(Continued)

FOREIGN PATENT DOCUMENTS

KR    10-2021-0064483    6/2021

*Primary Examiner* — Ryan A Lubit
(74) *Attorney, Agent, or Firm* — F. Chau & Associates, LLC

(57) ABSTRACT

A display device includes display pixels arranged in a display area of a display panel, light-sensing pixels arranged alternately with the display pixels in the display area, light-sensing scan lines, each divided into at least two horizontal lines disposed adjacent to each other and connected to light-sensing pixels disposed proximate to the at least two horizontal lines, a display scan driver configured to sequentially supply display scan signals to display pixels connected to each horizontal line through display scan lines corresponding to each horizontal line, a blood-pressure detecting circuit configured to measure a user's blood pressure using light-sensing signals input through the light-sensing pixels, and a display driving circuit configured to control a timing at which the display scan signals are supplied to the display scan lines and a timing at which sensing scan signals are supplied to the light-sensing scan lines.

20 Claims, 26 Drawing Sheets

(51) Int. Cl.
    *A61B 5/024*      (2006.01)
    *G06F 3/041*      (2006.01)
    *G09G 3/3233*    (2016.01)
    *G06F 3/044*      (2006.01)
    *G09G 3/20*       (2006.01)

(52) U.S. Cl.
    CPC ... *G09G 3/2007* (2013.01); *G09G 2300/0819* (2013.01); *G09G 2300/0842* (2013.01); *G09G 2310/0213* (2013.01); *G09G 2310/08* (2013.01); *G09G 2354/00* (2013.01); *G09G 2360/14* (2013.01); *G09G 2380/08* (2013.01)

(56) References Cited

U.S. PATENT DOCUMENTS

| | | | | |
|---|---|---|---|---|
| 2012/0262384 | A1* | 10/2012 | Kim | G06F 3/04184 |
| | | | | 345/173 |
| 2019/0008399 | A1* | 1/2019 | Mukkamala | A61B 5/0261 |
| 2019/0391702 | A1* | 12/2019 | Jo | G06F 3/0412 |
| 2020/0163561 | A1* | 5/2020 | Choe | A61B 5/02125 |
| 2021/0067618 | A1* | 3/2021 | Hong | A61B 5/6898 |
| 2021/0157441 | A1* | 5/2021 | Chen | G06F 3/0412 |
| 2021/0158751 | A1* | 5/2021 | Cha | G06V 40/1318 |
| 2023/0200668 | A1* | 6/2023 | Reynolds | A61B 5/6898 |
| | | | | 600/490 |

* cited by examiner

USPX: SPX1, SPX2, XPX3, LSP

DISPLAY DEVICE

CROSS-REFERENCE TO RELATED APPLICATIONS

This application claims priority under 35 U.S.C. § 119 to Korean Patent Application No. 10-2022-0070505, filed on Jun. 10, 2022 in the Korean Intellectual Property Office, the disclosure of which is incorporated by reference herein in its entirety.

TECHNICAL FIELD

Embodiments of the present disclosure relate to a display device.

DISCUSSION OF RELATED ART

As an information-oriented society evolves, various demands for display devices are ever increasing. Display devices are being employed by a variety of electronic devices such as smartphones, digital cameras, laptop computers, table PCs, navigation devices, and smart televisions. Portable display devices such as smartphones and tablet PCs may be equipped with a variety of features including image capturing, fingerprint recognition, facial recognition, etc.

As the healthcare industry continues to evolve, methods for acquiring biometric information more conveniently are being developed. For example, there is an attempt to apply a traditional oscillometric blood pressure measurement device to a portable blood pressure measurement device.

SUMMARY

Aspects of the present disclosure provide a display device capable of detecting a photoplethysmography signal using an image display panel and measuring a user's blood pressure.

Aspects of the present disclosure also provide a display device capable of detecting light-sensing signals at a high speed equal to or similar to the driving frequency of the image display panel, and detecting pulse wave signals according to the light-sensing signals without an error due to the detection speed or frequency of the light-sensing signals.

According to an embodiment of the disclosure, a display device includes display pixels arranged in a display area of a display panel, light-sensing pixels alternately arranged with the display pixels in the display area, light-sensing scan lines each divided into at least two horizontal lines disposed adjacent to each other and connected to light-sensing pixels among the light-sensing pixels disposed proximate to the at least two horizontal lines, a display scan driver configured to sequentially supply display scan signals to display pixels connected to each horizontal line through display scan lines corresponding to each horizontal line, a blood-pressure detecting circuit configured to measure a user's blood pressure using light-sensing signals input through the light-sensing pixels, and a display driving circuit configured to control a timing at which the display scan signals are supplied to the display scan lines and a timing at which sensing scan signals are supplied to the light-sensing scan lines.

In an embodiment, the display scan driver supplies (2i-j)th display scan signals among the display scan signals to the light-sensing scan lines connected to the light-sensing pixels for each of the at least two horizontal lines. The light-sensing pixels output the light-sensing signal in response to the (2i-j)th display scan signals, where i is a positive integer and j is a positive integer equal to or different from i.

In an embodiment, each of the display pixels includes a light-emitting element and a pixel driving unit connected to the light-emitting element. Each of the light-sensing pixels includes a photo-detecting element and a sensing driving unit connected to the photo-detecting element. The pixel driving unit receives ith display scan signals from among the display scan signals sequentially supplied through the display scan lines, and the sensing driving unit receives the (2i-j)th display scan signals and outputs the light-sensing signal to the blood-pressure detecting circuit.

In an embodiment, red, green and blue display pixels among the display pixels of the display area and one light-sensing pixel form a unit pixel. The red, green, and blue display pixels and the one light-sensing pixel are repeatedly and sequentially arranged in horizontal or vertical stripes along first and second directions of the display area.

In an embodiment, the display device further includes a light-sensing driver configured to sequentially generate sensing scan signals for each horizontal line in response to a light-sensing control signal received from the display driving circuit, and to sequentially supply (2i-j)th sensing scan signals among the sensing scan signals to the light-sensing scan lines. The display scan driver sequentially supplies display scan signals to the display pixels for each horizontal line in response to a write control signal from the display driving circuit, and i is a positive integer equal to or different from i.

In an embodiment, each of the light-sensing pixels includes a photo-detecting element and a sensing driving unit connected to the photo-detecting element, and the sensing driving unit receives the $2(i\text{-}j)$th sensing scan signals and outputs the light-sensing signals to the blood-pressure detecting circuit.

In an embodiment, the display device further includes a pressure sensing unit disposed on a front side of the display panel and configured to sense pressure applied by a user's body part and output a pressure sensing signal, a touch sensing unit disposed on a front side of the pressure sensing unit and configured to sense a user's touch and output a touch sensing signal, and a touch driver configured to generate pressure data and pressure sensing coordinate data according to a change in a magnitude of the pressure sensing signal and a first output position, and to generate touch data and touch coordinate data according to a change in magnitude of the touch sensing signal and a second output position.

In an embodiment, the display driving circuit detects and sets a touch area touched by the body part based on the touch coordinate data, arranges predetermined grayscale data for blood pressure sensing to match a position of the touch area and supplies the predetermined grayscale data to the data driver, and supplies the write control signal to the display scan driver to control display pixels in the touch area to emit light, and supplies the light-sensing control signal to the light-sensing driver such that the (2i-j)th sensing scan signals are sequentially supplied to the light-sensing pixels.

In an embodiment, the display driving circuit supplies coordinate information corresponding to the touch area to the blood-pressure detecting circuit, and the blood-pressure detecting circuit receives the light-sensing signals through each of a plurality of sensing drivers associated with the touch area based on the coordinate information corresponding to the touch area, and detects a pulse wave signal and a blood pressure of the user.

In an embodiment, the display panel further includes sensing reset lines each divided into at least two additional horizontal lines disposed adjacent to each other and connected to light-sensing pixels among the light-sensing pixels disposed proximate to the at least two additional horizontal lines, and the light-sensing driver sequentially generates sensing reset signals for each horizontal line in response to the light-sensing signal received from the display driving circuit, and sequentially supplies (2i-j)th sensing reset signals among the sensing reset signals to the sensing reset lines.

In an embodiment, each of the light-sensing pixels includes a photo-detecting element and a sensing driving unit connected to the photo-detecting element, and the light-sensing driver is reset in response to the (2i-j)th sensing reset signals, and outputs the light-sensing signal to the blood-pressure detecting circuit in response to the (2i-j)th sensing scan signals supplied after the light-sensing driver is reset.

In an embodiment, each of the light-sensing scan lines and the sensing reset lines is branched into a plurality of lines and is electrically connected to the light-sensing pixels in the at least two horizontal lines.

In an embodiment, the light-sensing pixels are electrically connected to one of the sensing reset lines, one of the light-sensing scan lines, and one of sensing lines arranged in the display area, are reset by the sensing reset signals received from the sensing reset lines, and transmits the light-sensing signals to the sensing lines in response to the sensing scan signals from the light-sensing scan lines.

In an embodiment, each of the light-sensing pixels includes a photo-detecting unit including a photo-detecting element, and a sensing driving unit including first to third sensing transistors and a sensing capacitor, and the sensing capacitor is connected in parallel with the photo-detecting element.

In an embodiment, the first sensing transistor allows a light-sensing current to flow to the second sensing transistor according to voltages of the photo-detecting element and the sensing capacitor, the third sensing transistor supplies a reset voltage to the photo-detecting element in response to the (2i-j)th sensing reset signals, and the second sensing transistor outputs the light-sensing signal of the photo-detecting element to a sensing line in response to the (2i-j)th sensing scan signals.

In an embodiment, a number of horizontal lines that allow the light-sensing pixels to receive a same sensing scan signal through the respective light-sensing scan lines is determined according to a ratio of a driving period of the light-sensing pixels for each horizontal line to a pulse wave signal detection and conversion period of the blood-pressure detecting circuit.

In an embodiment, the display device further includes a pressure sensing unit disposed on a front side of the display panel and configured to sense pressure applied by a user's body part and output a pressure sensing signal, a touch sensing unit disposed on a front side of the pressure sensing unit and configured to sense a user's touch and output a touch sensing signal, and a touch driver configured to generate pressure data and pressure sensing coordinate data according to a change in a magnitude of the pressure sensing signal and a first output position, and to generate touch data and touch coordinate data according to a change in magnitude of the touch sensing signal and a second output position.

In an embodiment, the display driving circuit detects and sets a touch area touched by the body part based on the touch coordinate data, arranges predetermined grayscale data for blood pressure sensing to match a position of the touch area and supplies the predetermined grayscale data to the data driver, supplies the write control signal to the display scan driver to control display pixels in the touch area to emit light, and supplies the light-sensing control signal to the light-sensing driver such that the (2i-j)th sensing scan signals are sequentially supplied to the light-sensing pixels.

In an embodiment, the display driving circuit supplies coordinate information corresponding to the touch area to the blood-pressure detecting circuit, and the blood-pressure detecting circuit receives the light-sensing signals through each of a plurality of sensing drivers associated with the touch area based on the coordinate information corresponding to the touch area, and detects a pulse wave signal and blood pressure of the user.

In an embodiment, a number of connections of at least two horizontal lines adjacent to each other to which the light-sensing scan lines are respectively connected is determined according to a ratio of a light-sensing driving period of the light-sensing pixels for each horizontal line to a pulse wave signal detection period of the blood-pressure detecting circuit.

According to embodiments of the present disclosure, when light output from an image display pixel is reflected by a part of the body such as a user's finger, the reflected light is sensed by a light-sensing pixel of the display panel, and is used to detect the user's blood pressure. In this manner, the user's blood pressure can be detected using the display panel of the display device.

According to embodiments of the present disclosure, distortion of the detected waveform of the light-sensing signals may be prevented or reduced by way of detecting the light-sensing signals at a frequency of about 100 Hz or higher, which is, e.g., a frequency that is equal to or similar to the driving frequency of the image display panel. In addition, by accurately detecting the pulse wave signals according to the light-sensing signals without errors due to the detection speed or the detection frequency of the light-sensing signals, the reliability of the blood-pressure detection function can be increased.

BRIEF DESCRIPTION OF THE DRAWINGS

The above and other aspects and features of the present disclosure will become more apparent by describing in detail embodiments thereof with reference to the accompanying drawings.

DETAILED DESCRIPTION OF THE EMBODIMENTS

Figure 1:
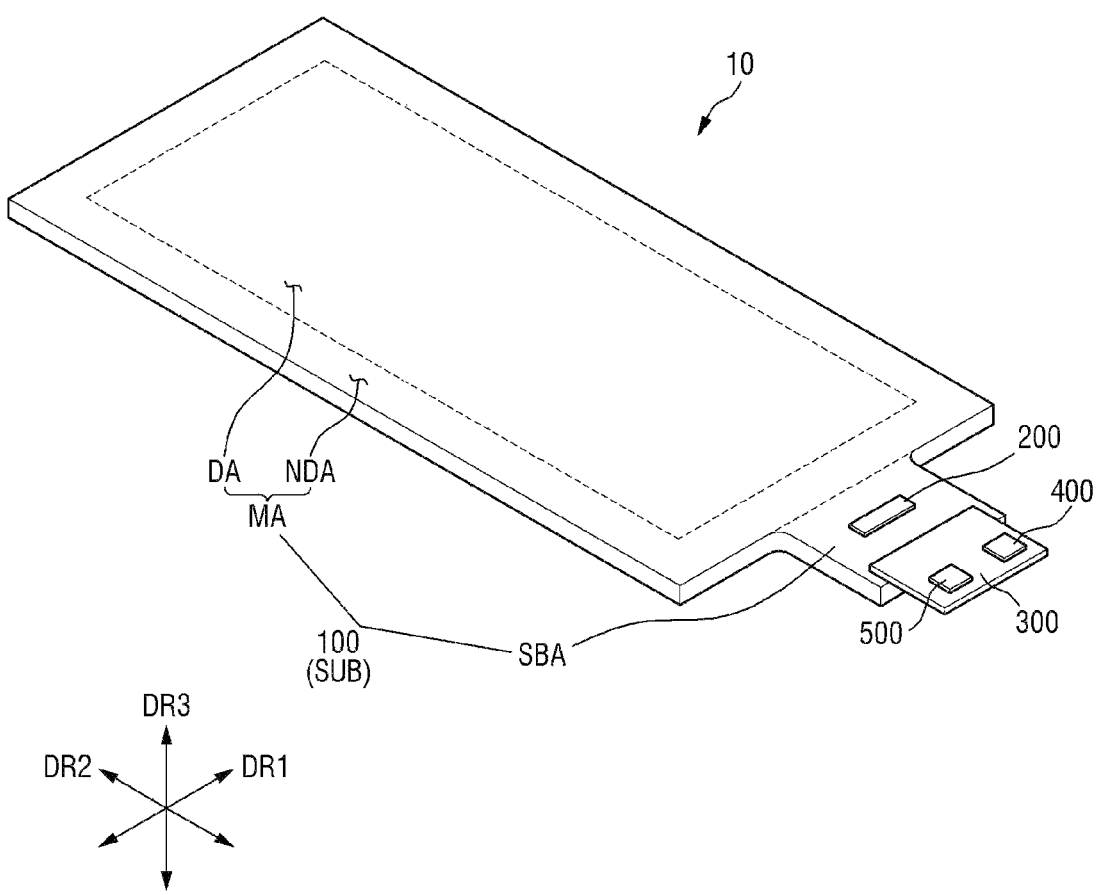
FIG. 1 is a perspective view of a display device according to an embodiment of the present disclosure.

Embodiments of the present disclosure will be described more fully hereinafter with reference to the accompanying drawings. Like reference numerals may refer to like elements throughout the accompanying drawings.

It will be understood that when a component such as a film, a region, a layer, etc., is referred to as being "on", "connected to", "coupled to", or "adjacent to" another component, it can be directly on, connected, coupled, or adjacent to the other component, or intervening components may be present. It will also be understood that when a component is referred to as being "between" two components, it can be the only component between the two components, or one or more intervening components may also be present. Other words used to describe the relationships between components should be interpreted in a like fashion.

It will be understood that, although the terms "first," "second," etc. may be used herein to describe various elements, these elements should not be limited by these terms. These terms are only used to distinguish one element from another element. For example, a first element discussed below could be termed a second element without departing from the teachings of the present invention, and similarly, the second element could also be termed the first element.

Each of the features of the various embodiments of the present disclosure may be combined or combined with each other, in part or in whole, and technically various interlocking and driving are possible. Each embodiment may be implemented independently of each other or may be implemented together in an association.

As used herein, the singular forms "a", "an" and "the" are intended to include the plural forms as well, unless the context clearly indicates otherwise.

It should be understood that descriptions of features or aspects within each embodiment should typically be considered as available for other similar features or aspects in other embodiments, unless the context clearly indicates otherwise.

Herein, when two or more elements or values are described as being substantially the same as or about equal to each other, it is to be understood that the elements or values are identical to each other, the elements or values are equal to each other within a measurement error, or if measurably unequal, are close enough in value to be functionally equal to each other as would be understood by a person having ordinary skill in the art. For example, the term "about" as used herein is inclusive of the stated value and means within an acceptable range of deviation for the particular value as determined by one of ordinary skill in the art, considering the measurement in question and the error associated with measurement of the particular quantity (e.g., the limitations of the measurement system). For example, "about" may mean within one or more standard deviations as understood by one of the ordinary skill in the art. Further, it is to be understood that while parameters may be described herein as having "about" a certain value, according to exemplary embodiments, the parameter may be exactly the certain value or approximately the certain value within a measurement error as would be understood by a person having ordinary skill in the art. Other uses of these terms and similar terms to describe the relationships between components should be interpreted in a like fashion.

Figure 2:
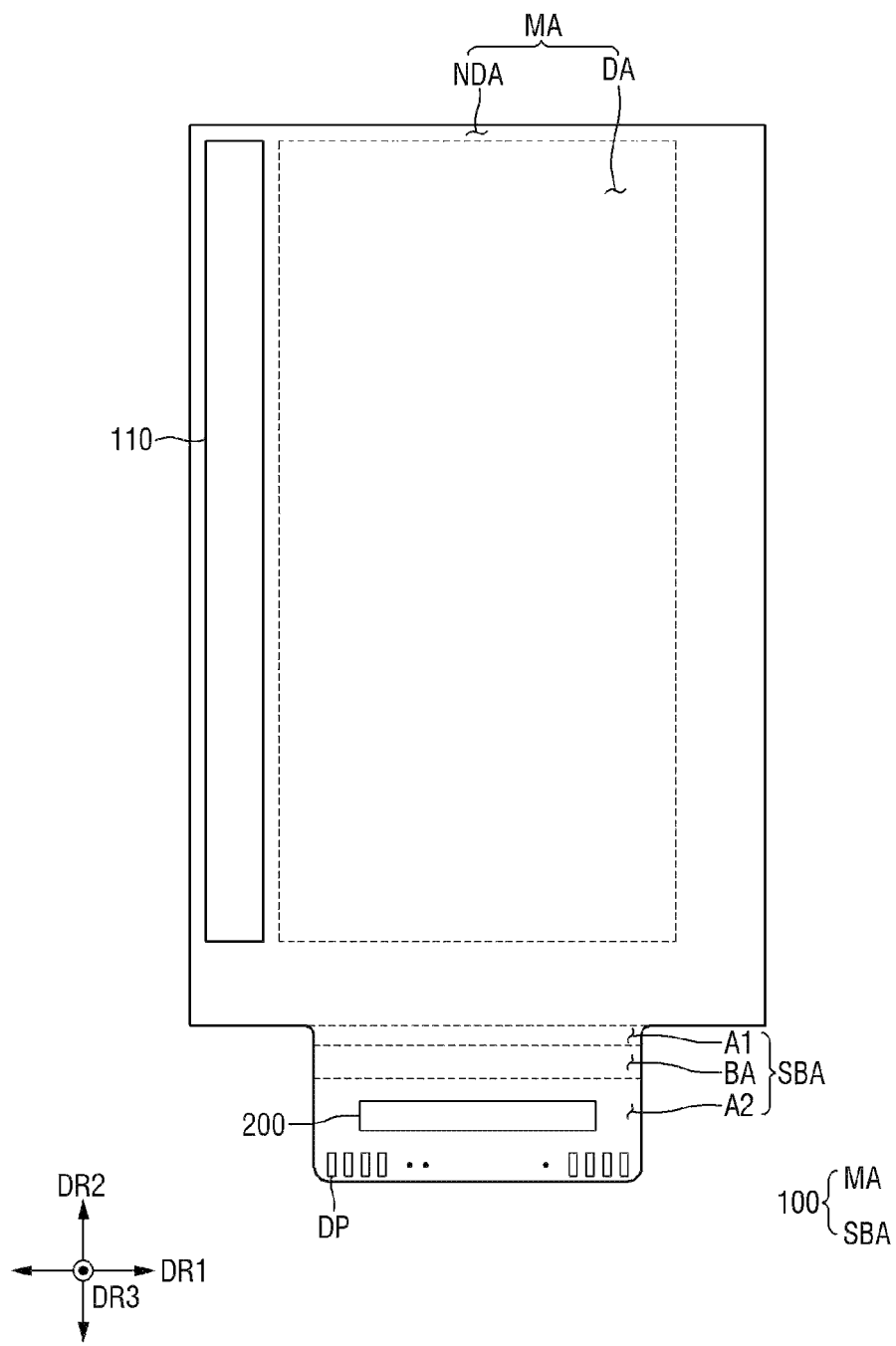
FIG. 2 is a plan view showing the arrangement structure of the display panel and the display driving circuit shown in FIG. 1 according to an embodiment of the present disclosure.
Figure 3:
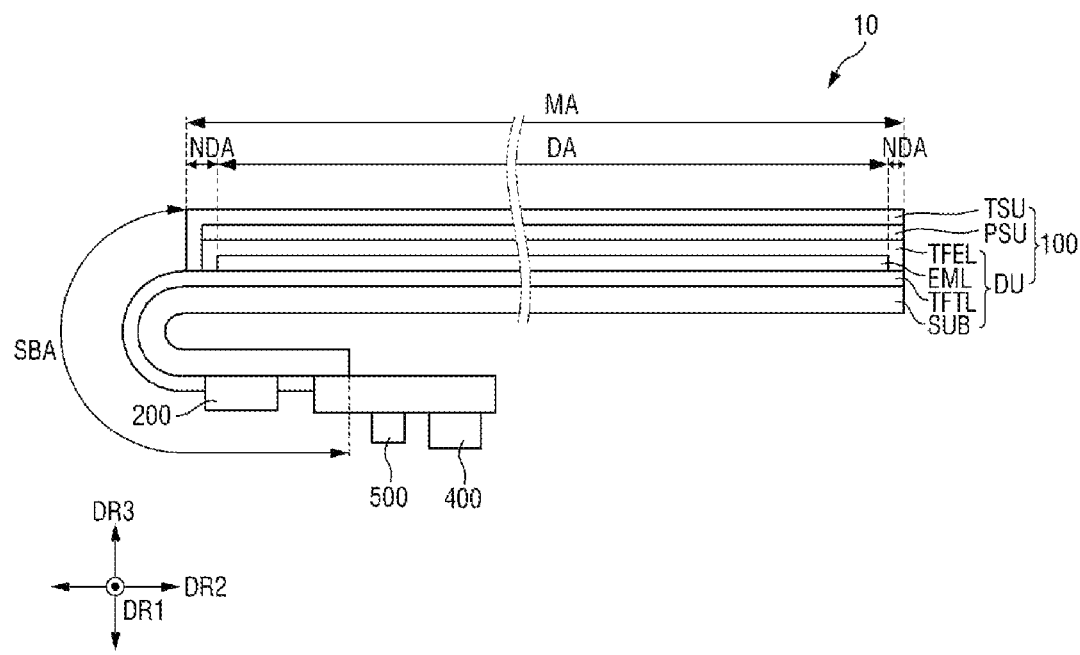
FIG. 3 is a cross-sectional view showing the configuration of the display device shown in FIG. 1 according to an embodiment of the present disclosure.

FIG. 1 is a perspective view of a display device according to an embodiment of the present disclosure. FIG. 2 is a plan view showing the arrangement structure of the display panel and the display driving circuit shown in FIG. 1 according to an embodiment of the present disclosure. FIG. 3 is a cross-sectional view showing the configuration of the display device shown in FIG. 1 according to an embodiment of the present disclosure.

Referring to FIGS. 1 and 2, a display device 10 according to an embodiment of the present disclosure may be utilized in portable electronic devices such as, for example, a mobile phone, a smartphone, a tablet PC, a mobile communications terminal, an electronic notebook, an electronic book, a portable multimedia player (PMP), a navigation device an ultra mobile PC (UMPC), etc. Alternatively, the display device 10 according to an embodiment of the present disclosure may be used as a display unit of, for example, a television, a laptop computer, a monitor, an electronic billboard, an Internet of Things (JOT) device, etc. Alternatively, the display device 10 according to an embodiment of the present disclosure may be applied to wearable devices such as, for example, a smartwatch, a watch phone, a glasses-type display, a head-mounted display (HMD) device, etc. Alternatively, the display device 10 according to an embodiment of the present disclosure may be used in a vehicle, for example, as a center information display (CID) disposed at an instrument cluster, the center fascia or the dashboard of a vehicle, as a room mirror display on the side mirrors of a vehicle, as a display placed on the back of each of the front seats (e.g., as part of an entertainment system for passengers at the rear seats of a vehicle), etc.

The display device 10 may be a light-emitting display device such as, for example, an organic light-emitting display device using organic light-emitting diodes, a quantum-dot light-emitting display device including a quantum-dot light-emitting layer, an inorganic light-emitting display device including an inorganic semiconductor, and an ultra-small light-emitting display device using micro or nano light-emitting diodes (micro LEDs or nano LEDs). In the following description, an organic light-emitting display device is described as an example of the display device 10. It is, however, to be understood that the present disclosure is not limited thereto.

Referring to FIGS. 1 and 3, the display device 10 includes a display panel 100, a display driving circuit 200, a touch sensing unit TSU, a pressure sensing unit PSU, a circuit board 300, a blood-pressure detecting circuit 400 and a touch driver 500.

The display panel 100 may be formed in a rectangular shape having shorter sides in a first direction DR1 and longer sides in a second direction DR2 intersecting the first direction DR1 when viewed from the top (when viewed in a plan view). Each of the corners where the shorter side in the first direction DR1 meets the longer side in the second direction DR2 may be formed at a right angle (or at about a right angle) or may be rounded with a predetermined curvature. The shape of the display panel 100 when viewed from the top is not limited to a quadrangular shape, but may be formed in a different polygonal shape, a circular shape, or an elliptical shape. The display panel 100 may be formed flat, but is not limited thereto. For example, the display panel 100 may be formed at left and right ends, and may include a curved portion having a constant curvature or a varying curvature. In addition, the display panel 100 may be flexible so that it can be curved, bent, folded or rolled.

A substrate SUB of the display panel 100 may include a main area MA and a subsidiary area SBA.

The main area MA may include a display area DA where images are displayed, and a non-display area NDA disposed around the display area DA where images are not displayed.

The non-display area NDA may be disposed adjacent to the display area DA. The non-display area NDA may be disposed on the outer side of the display area DA. The non-display area NDA may surround the display area DA. The non-display area NDA may be defined as the border of the display panel 100.

The display area DA includes display pixels that display images, and light-sensing pixels that sense light reflected off a part of a user's body, such as, for example, a finger. The display area DA may occupy most of the main area MA. The display area DA may be disposed at the center of the main area MR.

The display area DA may be divided into an image display area in which only display pixels are disposed without light-sensing pixels, and a blood-pressure detection area in which light-sensing pixels as well as display pixels are disposed. For example, the light-sensing pixels may be disposed together with the display pixels only in a predetermined part of the entire display area DA of the display panel 100, e.g., only in a blood-pressure sensing area. In the following description, it is assumed that the display pixels and the light-sensing pixels are alternately arranged in the entire display area DA.

Referring to FIGS. 2 and 3, the subsidiary area SBA may protrude from one side of the main area MA in the second direction DR2. The length of the subsidiary area SBA in the second direction DR2 may be smaller than the length of the main area MA in the second direction DR2. The length of the subsidiary area SBA in the first direction DR1 may be substantially less than the length of the main area MA in the first direction DR1 or may be substantially equal to the length of the main area MA in the first direction DR1.

The subsidiary area SBA may include a first area A1, a second area A2 and a bending area BA.

The first area A1 protrudes from one side of the main area MA in the second direction DR2. One side of the first area A1 may be in contact with the non-display area NDA of the main area MA (e.g., the one side of the first area A1 may be directly adjacent to the non-display area NDA such that a space or gap does not exist between the one side of the first area A1 and the non-display area NDA), and the opposite side of the first area A1 may be in contact with the bending area BA (e.g., the opposite side of the first area A1 may be directly adjacent to the bending area BA such that a space or gap does not exist between the opposite side of the first area A1 and the bending area BA).

Pads DP and the display driving circuit 200 are disposed in the second area A2. The display driving circuit 200 may be attached to driving pads of the second area A2 using a conductive adhesive member such as an anisotropic conductive film. The circuit board 300 may be attached to the pads DP of the second area A2 using a conductive adhesive member. One side of the second area A2 may be in contact with the bending area BA (e.g., the one side of the second area A2 may be directly adjacent to the bending area BA such that a space or gap does not exist between the one side of the second area A2 and the bending area BA).

The bending area BA is a part of the display panel 100 that is bendable. When the bending area BA is bent, the second area A2 may be disposed under the first area A1 and under the main area MA. The bending area BA may be disposed between the first area A1 and the second area A2. One side of the bending area BA may be in contact with the first area A1, and the opposite side of the bending area BA may be in contact with the second area A2.

As shown in FIG. 3, the subsidiary area SBA may be bent so that it is located under the main area MA. The subsidiary area SBA may overlap the main area MA in the thickness direction DR3. The display device 10 includes a display unit DU including a thin film encapsulation layer TFEL, a light-emitting element layer EML, and a thin film transistor layer TFTL.

The pressure sensing unit PSU, which may sense pressure applied by a part of the body such as a finger, may be disposed on the front surface of the display panel 100. The pressure sensing unit PSU may be formed as a transparent sheet in which transparent electrodes are arranged in vertical and horizontal directions, and may be disposed on the front surface of the main area MA.

The touch sensing unit TSU, which may sense a part of the body such as a finger, may be disposed on the front side of the pressure sensing unit PSU including the display area DA. The touch sensing unit TSU may include a plurality of touch electrodes which sense a user's touch by capacitive sensing.

The touch sensing unit TSU includes a plurality of touch electrodes arranged such that they cross each other in the first and second directions DR1 and DR2. For example, the plurality of touch electrodes includes a plurality of driving electrodes arranged in parallel and spaced apart from one another in the first direction DR1, and a plurality of sensing electrodes arranged in parallel and spaced apart from one another in the second direction DR2, the sensing electrodes crossing the driving electrodes with an organic material layer or an inorganic material layer disposed therebetween. The driving electrodes and the sensing electrodes may extend in a wiring area between the display pixels and the light-sensing pixels (or the non-display area where the lines are formed) so that they do not overlap the display pixels (SPX, see FIG. 4) or the light-sensing pixels (LSP, see FIG. 4) arranged in the display area DA. Such driving electrodes and sensing electrodes form a mutual capacitance, and transmit touch sensing signals that are changed according to a user's touch to the touch driver 500.

The touch driver 500 may supply touch driving signals to the plurality of driving electrodes, and may receive touch sensing signals from the plurality of sensing electrodes. The touch driver 500 may sense a change in mutual capacitance between the plurality of driving electrodes and the plurality of sensing electrodes based on a change in the magnitude of the touch sensing signals. In addition, the touch driver 500 may supply touch data according to a change in mutual capacitance and coordinate data of the position where the touch is sensed to the display driving circuit 200.

The pressure sensing unit TSU includes a plurality of pressure sensing electrodes arranged such that they cross each other in the first and second directions DR1 and DR2. For example, the plurality of pressure sensing electrodes includes a plurality of lower electrodes arranged in parallel and spaced apart from one another in the first direction DR1, and a plurality of upper electrodes arranged in parallel and spaced apart from one another in the second direction DR2, the upper electrodes crossing the lower electrodes with a transparent inorganic (or organic) material layer disposed therebetween. The lower electrodes and the upper electrodes may extend in a wiring area between display pixels and the photo-sensing pixels (or the non-display area where the lines are formed) so that they do not overlap the display pixels or the photo-sensing pixels arranged in the display area DA. Such lower electrodes and upper electrodes form a mutual capacitance with a transparent inorganic (or organic) material layer, and transmit pressure sensing signals that are changed according to a user's touch to the touch driver 500.

The touch driver 500 may receive pressure sensing signals from a plurality of lower electrodes or upper electrodes, and may sense a change in self-capacitance based on the pressure sensing signals. Accordingly, the touch driver 500 may supply the pressure data according to a change in the self-capacitance and the sensing coordinate data of the position where the pressure is sensed to the timing controller 220.

The circuit board 300 may be attached to one end of the subsidiary area SBA. Accordingly, the circuit board 300 may be electrically connected to the display panel 100 and the display driving circuit 200. The display panel 100 and the display driving circuit 200 may receive, for example, digital video data, timing signals, and driving voltages through the circuit board 300. The circuit board 300 may be, for example, a flexible printed circuit board, a printed circuit board, or a flexible film such as a chip-on film.

The display driving circuit 200 may generate digitizer data and electrical control signals used when driving the display panel 100. Each of the blood-pressure detecting circuit 400 and the touch driver 500 as well as the display driving circuit 200 may be implemented as an integrated circuit (IC). Each of the display driving circuit 200, the blood-pressure detecting circuit 400 and the touch driver 500 may be attached to the display panel 100 or the circuit board 300 by, for example, a chip on glass (COG) technique, a chip on plastic (COP) technique, or an ultrasonic bonding. It should be understood, however, that the present disclosure is not limited thereto. For example, the blood-pressure detecting circuit 400 and the touch driver 500 may be attached to the circuit board 300 by a chip on film (COF) technique.

Figure 4:
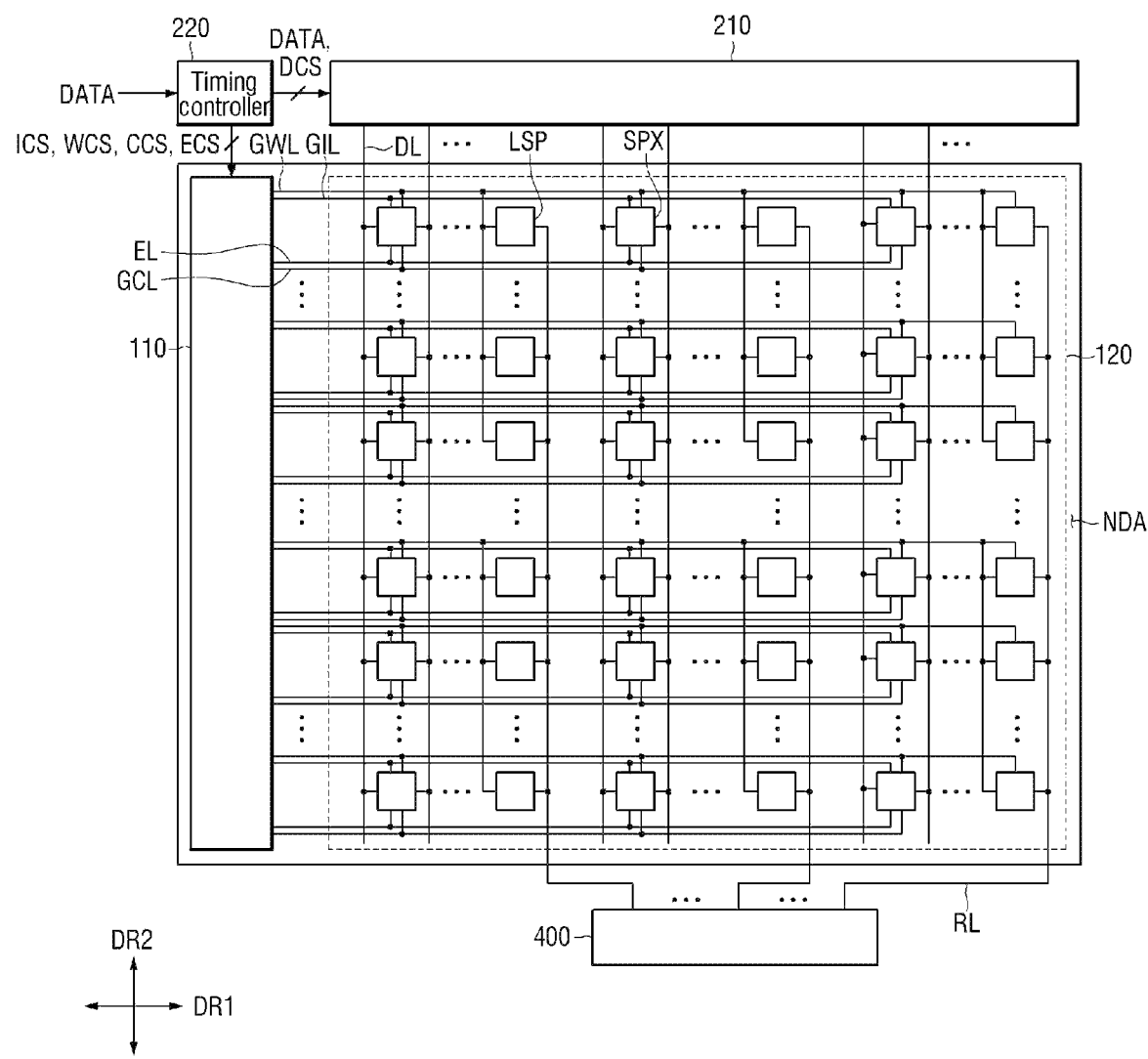
FIG. 4 is a block diagram showing in detail a display device according to an embodiment of the present disclosure.

FIG. 4 is a block diagram showing in detail a display device according to an embodiment of the present disclosure.

Referring to FIG. 4, the display device according to embodiments further includes a display panel 100, a display scan driver 110, a display driving circuit 200, a blood-pressure detecting circuit 400, a power supply, etc. The display driving circuit 200 may include a data driver 210 and a timing controller 220. In addition, the display driving circuit 200, the data driver 210 and the display scan driver 110 may be formed integrally and implemented as one-chip (1-chip) (e.g., as a single chip).

Referring to FIG. 4, the display panel 100 may include display pixels SPX, light-sensing pixels LSP, display write lines GWL, display initialization lines GIL, display control lines GCL, emission lines EL, data lines DL, and light-sensing lines RL, which are disposed in the display area DA. The display scan driver 110 is disposed in the non-display area NDA.

The display write lines GWL, the display initialization lines GIL, the display control lines GCL, and the emission lines EL may extend in the first direction DR1 (e.g., may extend lengthwise in the first direction DR1). The data lines DL and the light-sensing lines RL may extend in the second direction DR2 (e.g., may extend lengthwise in the second direction DR2).

The display pixels SPX and the light-sensing pixels LSP may be arranged in a matrix pattern in the first direction DR1 and the second direction DR2 in the display area DA. For example, three display pixels SPX that respectively display red, green, and blue lights and one light-sensing pixel LSP may form a single unit pixel. The red, green and blue display pixels SPX and the light-sensing pixel LSP forming each unit pixel may be repeatedly arranged in horizontal or vertical stripes. Each of the red, green and blue display pixels SPX may be connected to one of the display write lines GWL, one of the display initialization lines GIL, one of the display control lines GCL, and one of the emission lines EL. Each of the display pixels SPX may receive the data voltage from the data line DL in response to the display scan signal of the display write line GWL, the display initialization signal of the display initialization line GIL and the display control signal of the display control line GCL, and may supply a driving current to the light-emitting element according to the data voltage so that light is emitted.

The light-sensing pixels LSP may be alternately arranged with the red, green and blue display pixels SPX in the vertical or horizontal direction. Each of the light-sensing pixels LSP is connected to one of the display write lines GWL and one of the light-sensing lines RL. Each of the light-sensing pixels LSP transmits a light-sensing signal according to the amount of reflected light on the front surface to each light-sensing line RL in response to the display scan signal from the display write line GWL.

The display scan driver 110 may be disposed in the non-display area NDA. Although the display scan driver 110 is disposed on one side (e.g., the left side) of the display panel 100 in the drawings, embodiments of the present disclosure are not limited thereto. For example, the display scan driver 110 may be disposed on both sides (e.g., left and right sides) of the display panel 100 according to embodiments. The display scan driver 110 may be electrically connected to the display driving circuit 200 through scan fan-out lines. The display scan driver 110 may receive a write control signal WCS from the display driving circuit 200, may generate display scan signals according to the write control signal WCS, and may output the generated display scan signals to the display write lines GWL.

For example, the display scan driver 110 may be connected to the display write lines GWL, the display initialization lines GIL, the display control lines GCL, and the emission lines EL. The display scan driver 110 may include a display signal output that outputs display scan signals applied to the display write lines GWL, display initialization signals applied to the display initialization lines GIL and display control signals applied to the display control lines GCL, and an emission signal output that outputs emission signals applied to the emission lines EL.

The display scan driver 110 may receive a write control signal WCS, an initialization control signal ICS, a write control signal CCS and an emission control signal ECS from the timing controller 220. The display signal output of the display scan driver 110 may generate display control signals according to the sensing control signal SCS and may output the generated display control signals to the display write lines GWL. In addition, the display signal output of the display scan driver 110 may generate display initialization signals according to the initialization control signal ICS and may output the generated display initialization signals to the display initialization lines GIL. In addition, the display signal output of the display scan driver 110 may generate display control signals according to the write control signal CCS and may output the generated display control signals to the display control lines GCL. Moreover, the emission signal output of the display scan driver 110 may generate display emission signals according to the emission control signal ECS and may output the generated display emission signals to the display emission lines EL.

The data driver 210 converts digital video data DATA into data voltages and outputs the data voltages to the data lines DL. The data driver 210 may output data voltages in synchronization with the display scan signals. Therefore, the display pixels SPX are selected by the display scan signals of the display scan driver 110, and a data voltage may be applied to each of the selected display pixels SPX.

The timing controller 220 receives the digital video data DATA and timing signals from an external graphic device. For example, the external graphic device may be, but is not limited to, a graphic card of a computer, a set-top box, etc.

The timing controller 220 may generate the write control signal WCS, the initialization control signal ICS, the sensing control signal SCS and the emission control signal ECS, which are used to control the operation timing of the display scan driver 110 in response to the timing signals. In addition, the timing controller 220 may generate a data control signal DCS that controls the operation timing of the data driver 210 in response to the timing signals.

The timing controller 220 supplies the write control signal WCS, the initialization control signal ICS, the sensing control signal SCS and the emission control signal ECS to the display scan driver 110. In addition, the timing controller 220 may output the digital video data DATA and the data control signal DCS to the data driver 210.

The timing controller 220 may receive touch data from the touch driver 500 and may determine the coordinates of the user's touch using the touch data, and then may generate digitizer video data based on the coordinates or may execute an application indicated by the icon displayed at the coordinates of the user's touch. As another example, the timing controller 220 may receive pressure sensing data from the touch driver 500 and may use the pressure sensing data to determine the coordinates of the pressure sensing, and then may generate digitizer video data based on the coordinates of the pressure sensing or may execute an application indicated by the icon displayed at the coordinates of the pressure sensing. For example, the timing controller 220 may analyze the pressure sensing data from the pressure sensing unit PSU to detect the pressure applied by the user in real time, and may display the results of detecting the pressure applied by the user as a predetermined pressure display image.

The blood-pressure detecting circuit 400 receives a light-sensing signal input through at least one light-sensing line RL among the light-sensing lines RL. In addition, by calculating a pulse wave signal reflecting a blood change according to a heartbeat by using the light-sensing signal, the user's blood pressure can be measured based on the magnitude and change cycle of the pulse wave signal. A method of measuring blood pressure using the blood-pressure detecting circuit 400 will be described in more detail below.

Figure 5:
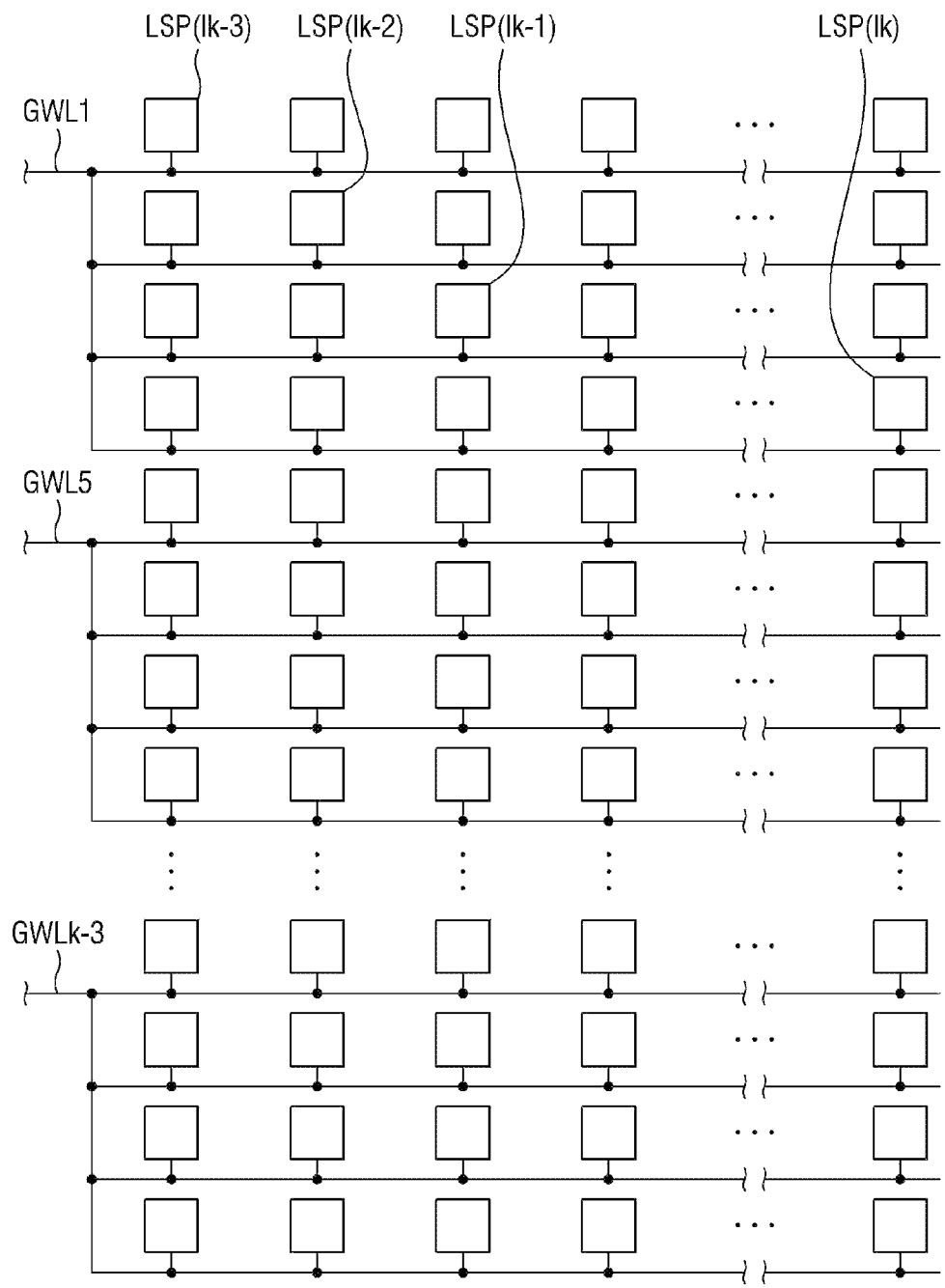
FIG. 5 is a diagram showing a connection structure of display write lines and light-sensing pixels of a display panel according to an embodiment of the present disclosure.

FIG. 5 is a diagram showing a connection structure of display write lines and light-sensing pixels of a display panel according to an embodiment.

The light-sensing pixels LSP arranged in the display area DA alternately with the red, green and blue display pixels SPX in a matrix pattern receive display scan signals through display write lines GWL, respectively.

For example, the light-sensing pixels LSP(lk−3) to LSP(lk) in the $(k-3)^{th}$ to $k^{th}$ horizontal lines arranged adjacent to one another are connected to the $(k-3)^{th}$ display write lines GWL1, GWL5, ... GWL(k−3), where k is an integer greater than three.

The light-sensing pixels LSP(lk−3) to LSP(lk) arranged in the $(k-3)^{th}$ to $k^{th}$ horizontal lines transmit the light-sensing signal according to the amount of reflected light on the front surface to the respective light-sensing lines RL in response to the $(k-3)^{th}$ display scan signal supplied through the $(k-3)^{th}$ display write line GWL1, GWL5, ... GWL(k−3).

Figure 6:
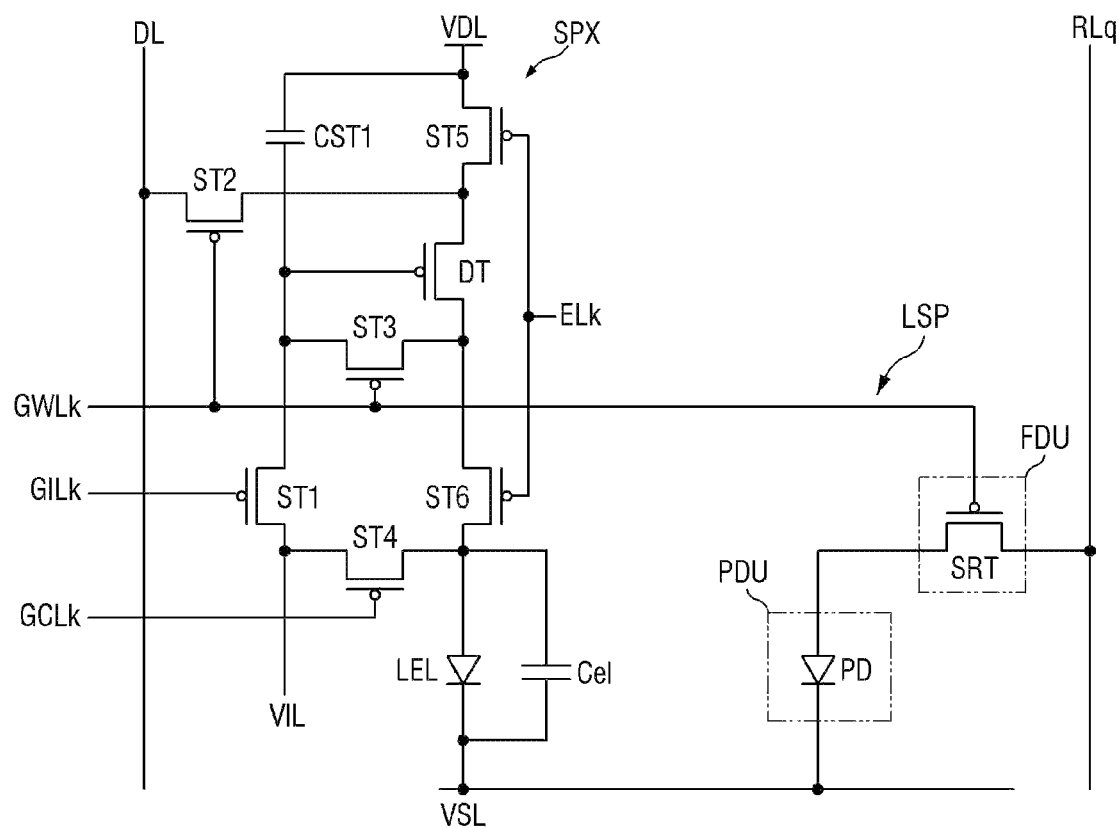
FIG. 6 is a circuit diagram showing a display pixel and a light-sensing pixel according to an embodiment of the present disclosure.

FIG. 6 is a circuit diagram showing a display pixel and a light-sensing pixel according to an embodiment of the present disclosure.

Referring to FIG. 6, each display pixel SPX according to an embodiment may be connected to the $k^{th}$ display initialization line GILk, the $k^{th}$ display write line GWLk, and the $k^{th}$ display control line GCLk. In addition, the display pixel SPX may be connected to a first supply voltage line VDL from which a first supply voltage is supplied, a second supply voltage line VSL from which a second supply voltage is supplied, and a third supply voltage line VIL from which a third supply voltage is supplied. In the following description, the letters such as k, j, i, p, n, m and q used in place of numbers are defined as positive integers excluding zero.

The display pixel SPX may include a light-emitting unit ELU and a pixel driving unit DDU. The light-emitting unit ELU may include a light-emitting element LEL. The pixel driving unit DDU may include a driving transistor DT, switch elements, and a capacitor CST1. The switch elements include first to sixth transistors ST1, ST2, ST3, ST4, ST5 and ST6.

The driving transistor DT may include a gate electrode, a first electrode and a second electrode. A drain-source current Ids (hereinafter referred to as "driving current") of driving transistor DT flowing between the first electrode and the second electrode is controlled according to the data voltage applied to the gate electrode. The driving current Ids flowing through the channel of the driving transistor DT is proportional to the square of the difference between a voltage Vsg between the first electrode and the gate electrode of the driving transistor DT and the threshold voltage, as shown in Equation 1 below:

$$Ids = k' \times (Vsg - Vth)^2 \qquad \text{[Equation 1]}$$

where k' denotes a proportional coefficient determined by the structure and physical properties of the driving transistor, Vsg denotes the voltage between the first electrode and the gate electrode of the driving transistor, and Vth denotes the threshold voltage of the driving transistor.

The light-emitting element LEL emits light as the driving current Ids flows therein. The amount of the light emitted from the light-emitting elements LEL may increase with the driving current Ids.

The light-emitting element LEL may be an organic light-emitting diode including an organic emissive layer disposed between an anode electrode and a cathode electrode. Alternatively, the light-emitting element LEL may be an inorganic light-emitting element including an inorganic semiconductor disposed between an anode electrode and a cathode electrode. Alternatively, the light-emitting element LEL may be quantum-dot light-emitting element including a quantum-dot emissive layer disposed between an anode electrode and a cathode electrode. Alternatively, the light-emitting element LEL may be a micro light-emitting element including a micro light-emitting diode disposed between an anode electrode and a cathode electrode.

The anode electrode of the light-emitting element LEL may be connected to the first electrode of the fourth transistor ST4 and the second electrode of the sixth transistor ST6, while the cathode electrode thereof may be connected to the second supply voltage line VSL. A parasitic capacitance Cel may be formed between the anode electrode and the cathode electrode of the light-emitting element LEL.

The first transistor T1 is turned on by an initialization scan initialization signal of the $k^{th}$ display initialization line GILk to connect the gate electrode of the driving transistor DT to the third supply voltage line VIL1. Accordingly, a third supply voltage VINT1 of the third supply voltage line VIL1 may be applied to the gate electrode of the driving transistor DT. The gate electrode of the first transistor ST1 may be connected to the $k^{th}$ display initialization line GILk, the first electrode thereof may be connected to the gate electrode of the driving transistor DT, and the second electrode thereof may be connected to the third supply voltage line VIL.

The second transistor ST2 is turned on by the display scan signal of the $k^{th}$ display write line GWLk to connect the first electrode of the driving transistor DT to the $j^{th}$ data line Dj. Accordingly, the data voltage of the $j^{th}$ data line Dj may be applied to the first electrode of the driving transistor DT. A gate electrode of the second transistor ST2 may be connected to the $k^{th}$ display write line GWLk, a first electrode thereof may be connected to the first electrode of the driving transistor DT, and a second electrode thereof may be connected to the $j^{th}$ data line Dj.

The third transistor ST3 is turned on by a display scan signal of the $k^{th}$ display write line GWLk to connect the gate electrode with the second electrode of the driving transistor DT. When the gate electrode and the second electrode of the driving transistor DT are connected to each other, the driving transistor DT works as a diode. A gate electrode of the third transistor ST3 may be connected to the $k^{th}$ display write line GWLk, a first electrode thereof may be connected to the second electrode of the driving transistor DT, and a second electrode thereof may be connected to the gate electrode of the driving transistor DT.

The fourth transistor ST4 is turned on by a display control signal of the $k^{th}$ display control line GCLk to connect the anode electrode of the light-emitting element LEL to the third supply voltage line VIL. The third supply voltage of the third supply voltage line VIL may be applied to the anode electrode of the light-emitting element LEL. The gate electrode of the fourth transistor ST4 may be connected to the $k^{th}$ display control line GCLk, the first electrode thereof may be connected to the anode electrode of the light-emitting element LEL, and the second electrode thereof may be connected to the third supply voltage line VIL.

The fifth transistor ST5 is turned on by the emission signal of a $k^{th}$ emission line ELk to connect the first electrode of the driving transistor DT to the first supply voltage line VDL. The gate electrode of the fifth transistor ST5 is connected to the $k^{th}$ emission line Ek, the first electrode thereof is connected to the first supply voltage line VDL, and the second electrode thereof is connected to the first electrode of the driving transistor DT.

The sixth transistor ST6 is disposed between the second electrode of the driving transistor DT and the anode electrode of the light-emitting element LEL. The sixth transistor ST6 is turned on by the emission control signal of the $k^{th}$ emission line ELk to connect the second electrode of the driving transistor DT to the anode electrode of the light-emitting element LEL. The gate electrode of the sixth transistor ST6 is connected to the $k^{th}$ emission line ELk, the first electrode thereof is connected to the second electrode of the driving transistor DT, and the second electrode thereof is connected to the anode electrode of the light-emitting element LEL.

When both the fifth transistor ST5 and the sixth transistor ST6 are turned on, the driving current Ids of the driving transistor DT according to the data voltage applied to the gate electrode of the driving transistor DT may flow to the light-emitting element LEL.

The capacitor CST1 is formed between the gate electrode of the driving transistor DT and the first supply voltage line VDL. The first capacitor electrode of the capacitor CST1 may be connected to the gate electrode of the driving transistor DT, and the second capacitor electrode thereof may be connected to the first supply voltage line VDL.

When the first electrode of each of the first to sixth transistors ST1, ST2, ST3, ST4, ST5 and ST6 and the driving transistor DT is a source electrode, the second electrode thereof may be a drain electrode. Alternatively, when the first electrode of each of the first to sixth transistors ST1, ST2, ST3, ST4, ST5 and ST6 and the driving transistor DT is a drain electrode, the second electrode thereof may be a source electrode.

The active layer of each of the first to sixth transistors ST1, ST2, ST3, ST4, ST5 and ST6 and the driving transistor DT may be formed of one of, for example, poly silicon, amorphous silicon and oxide semiconductor. Although the first to sixth transistors ST1, ST2, ST3, ST4, ST5 and ST6 and the driving transistor DT are implemented as p-type metal oxide semiconductor field effect transistors (MOSFETs) in FIG. 6, this is merely illustrative, and embodiments are not limited thereto. For example, in an embodiment, the first to sixth transistors ST1, ST2, ST3, ST4, ST5 and ST6 and the driving transistor DT may be implemented as n-type MOSFETs. Alternatively, in an embodiment, at least one of the first to sixth transistors ST1, ST2, ST3, ST4, ST5 and ST6 may be implemented as an n-type MOSFET.

According to an embodiment of the present disclosure, each light-sensing pixel LSP may be connected to the $k^{th}$ display write line GWLk and the $q^{th}$ light-sensing line RLq.

The light-sensing pixel LSP may include a photo-detecting unit PDU and a sensing driving unit FDU. The photo-detecting unit PDU may include a photo-detecting element PD. The sensing driving unit FDU may include a sensing signal transistor SRT.

The voltage at the sensing anode electrode of the photo-detecting element PD may vary depending on the amount of light incident on the photo-detecting element PD. For example, as the amount of light incident on the photo-detecting element PD increases, the voltage at the sensing anode electrode of the photo-detecting element PD may increase.

The photo-detecting element PD may be a photodiode including an anode electrode, a PIN semiconductor layer, and a cathode electrode. The sensing anode electrode of the photo-detecting element PD may be connected to the first electrode of the sensing signal transistor SRT, and the cathode electrode thereof may be connected to the second supply voltage line VSL. A p-i-n semiconductor layer of the photo-detecting element PD may include a p-type semiconductor layer connected to the anode electrode, an n-type semiconductor layer connected to the cathode electrode, and an i-type semiconductor layer disposed between the p-type semiconductor layer and the n-type semiconductor layer. In this instance, the i-type semiconductor layer is depleted by the p-type semiconductor layer PL and the n-type semiconductor layer NL so that an electric field is generated therein. The holes and electrons generated by light are drifted by the electric field. As a result, the holes may be collected to the anode electrode through the p-type semiconductor layer, and the electrons may be collected to the cathode electrode through the n-type semiconductor layer.

The sensing signal transistor SRT is turned on by the display scan signal of the $k^{th}$ display write line GWLk to connect the sensing anode electrode of the photo-detecting element PD with the $q^{th}$ light-sensing line RLq. Accordingly, the voltage at the sensing anode electrode of the photo-detecting element PD may be applied to the $q^{th}$ light-sensing line RLq. The gate electrode of the sensing signal transistor SRT may be connected to the $k^{th}$ display write line GWLk, the first electrode thereof may be connected to the sensing anode electrode of the photo-detecting element PD, and the second electrode thereof may be connected to the $q^{th}$ light-sensing line RLq.

Figure 7:
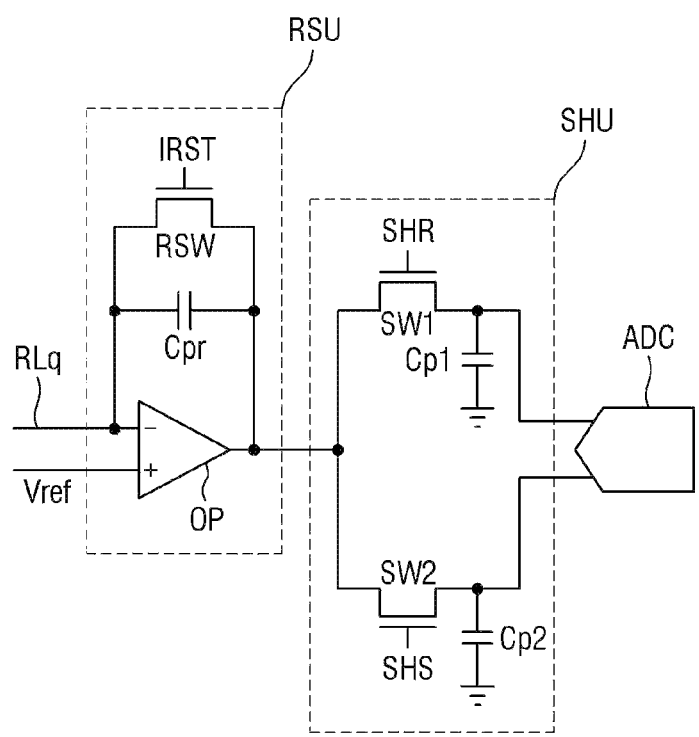
FIG. 7 is a circuit diagram showing a pulse wave signal converter of a blood-pressure detecting circuit according to an embodiment of the present disclosure.

FIG. 7 is a circuit diagram showing a pulse wave signal converter of a blood-pressure detecting circuit according to an embodiment of the present disclosure.

Referring to FIG. 7, the blood-pressure detecting circuit 400 includes a plurality of pulse wave signal converters that sample and digitally convert the light-sensing signals input through the respective $q^{th}$ light-sensing lines RLq to detect and generate pulse wave signals.

Each of the pulse wave signal converters includes a buffer unit RSU, a sampling unit SHU, and an AD converting unit ADC.

The buffer unit RSU is reset in response to a reset control signal IRST received from the display driving circuit 200 or amplifies and detects a light-sensing signal input through the $q^{th}$ light-sensing line RLq. The buffer unit RSU may include an operational amplifier OP, a reset switch RSW, and a reset capacitor Cpr. The operational amplifier OP amplifies and outputs the light-sensing signal. The reset switch RSW electrically connects the input terminal to the output terminal of the operational amplifier OP in response to the reset control signal IRST. The reset capacitor Cpr may be electrically connected between the input terminal and the output terminal of the operational amplifier OP to charge/discharge a feedback voltage.

The sampling unit SHU holds the light-sensing signal input from the stabilization buffer unit RSU in response to a holding control signal SHR from the display driving circuit 200 and outputs the held light-sensing signal in response to a sampling control signal SHS.

The sampling unit SHU includes a holding switch SW1, a holding capacitor Cp1, a sampling switch SW2, and a sampling capacitor Cp2.

The holding switch SW1 is connected in series between the light-sensing signal output terminal of the buffer unit RSU and the AD converting unit ADC, and holds the light-sensing signal input from the stabilization buffer unit RSU by the holding capacitor Cp1 in response to the holding control signal SHR. The sampling switch SW2 is connected in parallel with the holding switch SW1. The sampling switch SW2 allows the held sensing signal to be charged and sampled in the sampling capacitor Cp2 in response to the sampling control signal SHS.

The AD converting unit ADC converts the light-sensing signal output through the sampling unit SHU, e.g., the analog light-sensing signal charged and sampled by the sampling capacitor Cp2 into a digital signal, thereby detecting and outputting pulse wave signals. The AD converting unit ADC may include an AD converter.

The pulse wave signal converters of the blood-pressure detecting circuit 400 may be formed such that they are associated with the $q^{th}$ light-sensing lines RLq, respectively. A period in which the light-sensing signals are sampled and converted into a digital pulse wave signal through the pulse wave signal converters may be about 12.8 μs. For example, considering that the driving period of the display pixel SPX and the photo-sensing pixel LSP of one horizontal line is about 3.47 μs, the period in which the light-sensing signals are sampled and converted into a digital pulse wave signal may be about four horizontal periods. Accordingly, if the display pixel SPX and the light-sensing pixel LSP for each horizontal line are driven at a high speed of about 3.47 μs or more according to the driving frequency of about 100 Hz or higher, the light-sensing signals of two or more horizontal lines may be held or sampled in a holding period or a sampling period of the pulse wave signal converters. As a result, there may be light-sensing signal input error due to high-speed driving of the light-sensing pixels LSP.

In view of the above, according to an embodiment of the present disclosure, the light-sensing pixels LSP arranged on a plurality of adjacent horizontal lines output respective light-sensing signals in response to the same display scan signal input through the same display write line according to a ratio of the driving period of the light-sensing pixels LSP for each horizontal line (e.g., about 3.47 µs) to the pulse wave signal detection and conversion period of the pulse wave signal converters (e.g., about 12.8 µs), which may prevent an error that may occur if light-sensing signals of different magnitudes are input from the plurality of light-sensing pixels LSP during the pulse wave signal detection and conversion period of the pulse wave signal converters.

For example, the light-sensing pixels LSP(lk−3) to LSP (lk) of the $(k-3)^{th}$ to $k^{th}$ horizontal lines may output the light-sensing signals simultaneously in response to the same display scan signal input through one of the $(k-3)^{th}$ display write lines GWL1, GWL5, . . . GWL(k−3). Accordingly, the light-sensing pixels LSP(lk−3) to LSP(lk) of the $(k-3)^{th}$ to $k^{th}$ horizontal lines may output the light-sensing signals once during the pulse wave signal detection and conversion period of the pulse wave signal converters (e.g., about 12.8 µs). Then, the pulse wave signal converters may detect the pulse wave signals using the light-sensing signals input once during the pulse wave signal detection and conversion period (e.g., about 12.8 µs).

As described above, the number of horizontal lines that allows the light-sensing pixels LSP to receive the same display scan signal through the display write line may be determined based on the ratio of the driving period of the light-sensing pixels LSP for each horizontal line (e.g., about 3.47 µs) to the pulse wave signal detection and conversion period of the pulse wave signal converters (e.g., about 12.8 µs).

Figure 8:
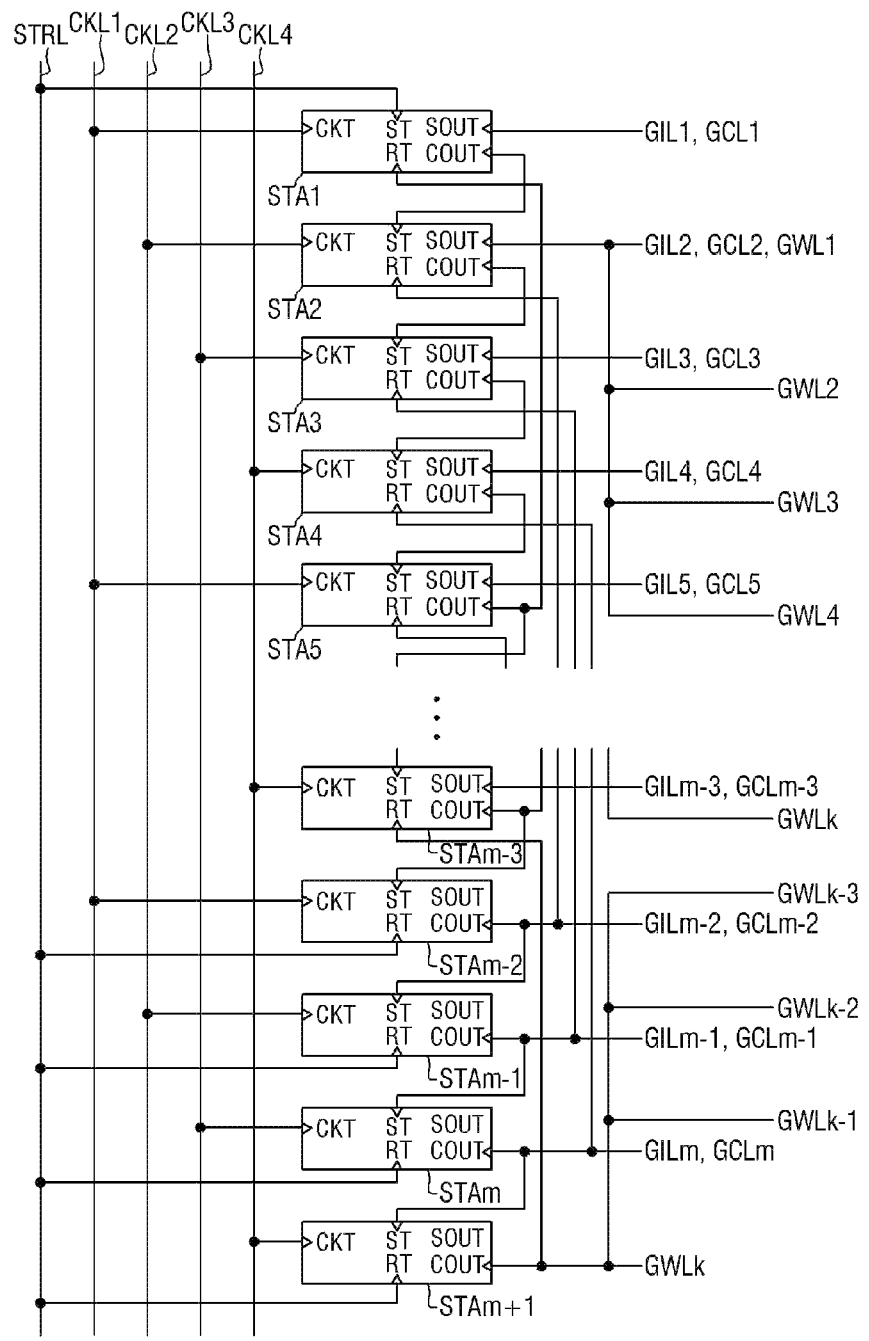
FIG. 8 is a view showing an example of the display scan driver according to an embodiment of the present disclosure.

FIG. 8 is a view showing an example of the display scan driver according to an embodiment of the present disclosure.

Referring to FIG. 8, the display scan driver 110 may include a plurality of display stages STA1, STA2, STA3, STA4, . . . , STA(m−1), STAm and STA(m+1), where m is a positive integer. Each of the plurality of display stages STA1, STA2, STA3, STA4, . . . , STA(m−1), STAm and STA(m+1) includes a start signal input ST, a reset signal input RT, a clock signal input CKT, a display signal output SOUT and a carry signal output COUT.

The start signal input ST of each of the plurality of display stages STA1, STA2, STA3, STA4, . . . , STA(m−1), STAm and STA(m+1) may be connected to a start line STRL or the carry signal output COUT of the previous display stage. For example, the start signal input ST of the first display stage STA1 may be connected to the display start line STRL from which the display start signal is input. In addition, the start signal input ST of each of the plurality of display stages STA2, STA3, STA4, . . . , STA(m−1), STAm and STA(m+1) except for the first display stage STA1 may be connected to the carry signal output COUT of the previous display stage. For example, the start signal input ST of the second display stage STA2 may be connected to the carry signal output COUT of the first display stage STA1, and the start signal input ST of the third display stage STA3 may be connected to the carry signal output COUT of the second display stage STA2.

The start signal input ST of each of the plurality of display stages STA1, STA2, STA3, STA4, . . . , STA(m−1), STAm and STA(m+1) may be connected to the carry signal output COUT of the subsequent display stage. For example, the reset signal input RT of the first display stage STA1 may be connected to the carry signal output COUT of the fifth display stage STA5.

The clock signal input CKT of each of the plurality of display stages STA1, STA2, STA3, STA4, . . . , STA(m−1), STAm and STA(m+1) may be connected to one of the clock lines CKL1, CKL2, CKL3 and CKL4.

The plurality of display stages STA1, STA2, STA3, STA4, . . . , STA(m−1), STAm and STA(m+1) may be connected to the clock lines CKL1, CKL2, CKL3 and CKL4 sequentially. For example, the clock signal input CKT of the first display stage STA1 may be connected to the first clock line CKL1, and the clock signal input CKT of the second display stage STA2 may be connected to the second clock line CKL2. The clock signal input CKT of the third display stage STA3 may be connected to the third clock line CKL3, and the clock signal input CKT of the fourth display stage STA4 may be connected to the fourth clock line CKL4.

The scan signal output SOUT of each of the plurality of display stages STA1, STA2, STA3, STA4, . . . , STA(m−1), STAm and STA(m+1) may be connected to the respective display write line, the respective display initialization line, and the respective display control line. For example, the first display stage STA1 may be connected to the first display initialization line GIL1 and the first display control line GCL1. In addition, the second display stage STA2 may be connected to a second display initialization line GIL2, a second display control line GCL2, and first to fourth display write lines GWL1 to GWL4.

As described above, the $(k-3)^{th}$ display write lines GWL1, GWL5, . . . GWL(k−3) may be electrically connected to the light-sensing pixels LSP(lk−3) to LSP(lk) arranged in the $(k-3)^{th}$ to $k^{th}$ horizontal lines, which are adjacent to one another. Accordingly, each of the $(k-3)^{th}$ display write lines GWL1, GWL5, . . . GWL(k−3) may extend or branch into the $(k-2)^{th}$, $(k-1)^{th}$ and $k^{th}$ display write lines GWL(k−2), GWL(k−1) and GWL(k−1).

In addition, the third display stage STA3 may be connected to a third display initialization line GIL3 and a third display control line GCL3. In addition, the fourth display stage STA4 may be connected to a fourth display initialization line GIL4 and a fourth display control line GCL4. In addition, the $(m-1)^{th}$ display stage STA(m−1) may be connected to the $(m-1)^{th}$ display initialization line GIL(m−1) and the $(m-1)^{th}$ display control line GCL(m−1). In addition, the mth display stage STAm may be connected to the mth display initialization line GILm.

The carry signal output COUT of each of the plurality of display stages STA1, STA2, STA3, STA4, . . . , STA(m−1), STAm and STA(m+1) may be connected to the reset signal input RT of the previous display stage and the start signal input ST of the subsequent display stage. In an embodiment, the carry signal output COUT of each of the first display stage STA1, the second display stage STA2, the third display stage STA3 and the fourth display stage STA4 may be connected only to the start signal input ST of the subsequent display stage.

Figure 9:
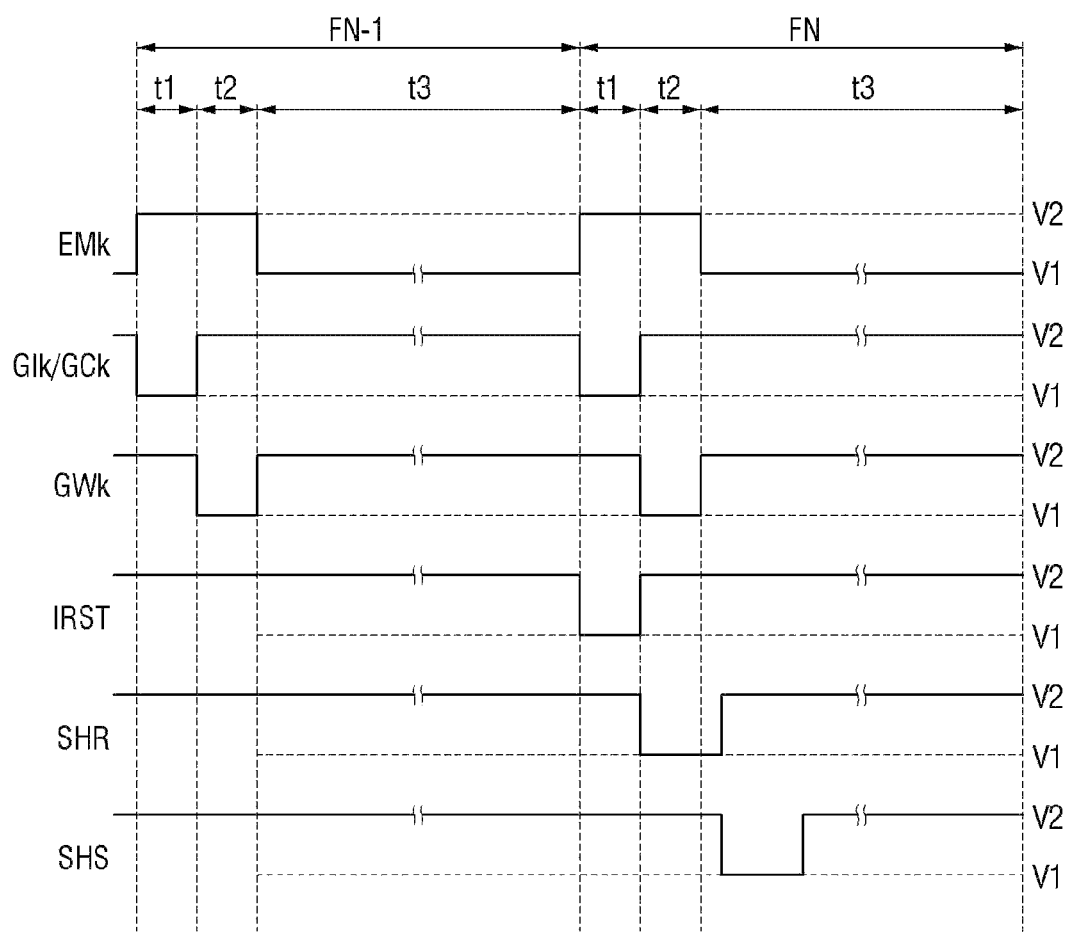
FIG. 9 is a waveform diagram showing scan signals input to a display pixel and a light-sensing pixel according to an embodiment of the present disclosure.

FIG. 9 is a waveform diagram showing scan signals input to a display pixel and a light-sensing pixel according to an embodiment of the present disclosure.

In FIG. 9, the $k^{th}$ display emission signal EMk applied to the $k^{th}$ display emission line ELk, the $k^{th}$ display initialization signal GIk applied to the $k^{th}$ display initialization line GILk, the $k^{th}$ display control signal GCk applied to the $k^{th}$ display control line GCLk, and the $k^{th}$ display scan signal GWk applied to the $k^{th}$ display write line GWLk during the $(n-1)^{th}$ frame period FN-1 and the nth frame period FN are shown.

The $k^{th}$ display initialization signal GIk is a signal that controls on-off of the first transistor ST1 of the display pixel SPX. The $k^{th}$ display control signal GCk is a signal that controls on-off of the fourth transistor ST4 of the display pixel SPX. The $k^{th}$ display scan signal GWk is a signal that controls on-off of the second transistor ST2, the third transistor ST3 and the sensing signal transistor SRT. The $k^{th}$ display emission signal EMk is a signal that controls on-off of the fifth transistor ST5 and the sixth transistor ST6.

Each of the $(n-1)^{th}$ frame period FN-1 and the nth frame period FN may include a first period t1, a second period t2, and a third period t3. During the first period t1, the gate electrode of the driving transistor DT is initialized to the third supply voltage VINT. During the second period t2, the data voltage is supplied to the gate electrode of the driving transistor DT, and the threshold voltage of the driving transistor DT is sampled. During the third period t3, the light-emitting element LEL emits light according to the gate voltage of the driving transistor DT. In addition, during the first period t1 and the third period t3, the photo-detecting element PD is exposed to light, and during the second period t2, the anode voltage of the photo-detecting element PD is sensed.

The $k^{th}$ display emission signal EMk has a first level voltage V1 during the third period t3 and has a second level voltage V2 during the first period t1 and the second period t2. The $k^{th}$ display scan signal GWk has the first level voltage V1 during the second period t2 and has the second level voltage V2 during the first period t1 and the third period t3.

The $k^{th}$ display initialization signal GIk and the $k^{th}$ display control signal GCk have the first level voltage V1 during the first period t1 and have the second level voltage V2 during the second period t2 and the third period t3. For example, the $k^{th}$ display initialization signal GIk may be substantially identical to the $k^{th}$ display control signal GCk.

Each of the first period t1 and the second period t2 may be one horizontal period. One horizontal period refers to a period in which a data voltage is applied to each of the display pixels SPX disposed in one horizontal line, and thus, one horizontal period may be defined as one horizontal line scan period. The display pixels SPX arranged in one horizontal line may be defined as sub-pixels connected to one display initialization line, one display write line, one display control line, and one emission line.

The first level voltage V1 may be a turn-on voltage capable of turning on the first to sixth transistors ST1, ST2, ST3, ST4, ST5 and ST6 and the sensing signal transistor SRT. The second level voltage V2 may be a turn-off voltage capable of turning off the first to sixth transistors ST1, ST2, ST3, ST4, ST5 and ST6 and the sensing signal transistor SRT. The second level voltage V2 may have a higher level than the first level voltage V1.

Hereinafter, operations of the display pixel SPX and the light-sensing pixel LSP during the first period t1, the second period t2 and the third period t3 will be described with reference to FIGS. 6 and 9.

Firstly, in the first period t1, the $k^{th}$ display initialization signal GIk having the first level voltage V1 is supplied to the $k^{th}$ display initialization line GILk, and the $k^{th}$ display control signal GCk having the first level voltage V1 is supplied to the $k^{th}$ display control wiring GCLk.

During the first period t1, the first transistor ST1 is turned on by the $k^{th}$ display initialization signal GIk having the first level voltage V1. As the first transistor ST1 is turned on, the third supply voltage VINT of the third supply voltage line VIL is applied to the gate electrode of the driving transistor DT. When the initialization voltage VINT is applied to the gate electrode of the driving transistor DT during the first period t1, the driving transistor DT may be turned on because the voltage Vsg between the first electrode and the gate electrode of the driving transistor DT is greater than the threshold voltage Vth of the driving transistor DT. For example, since an on-bias may be applied to the driving transistor DT, the hysteresis characteristics of the driving transistor DT may be improved according to embodiments of the present disclosure.

In addition, during the first period t1, the fourth transistor ST4 is turned on by the $k^{th}$ display control signal GCk having the first level voltage V1. Therefore, during the first period t1, as the fourth transistor ST4 is turned on, the anode electrode of the light-emitting element LEL may be initialized to the third supply voltage VINT of the third supply voltage line VIL.

Incidentally, during the first period t1, the $k^{th}$ display scan signal GWk having the second level voltage V2 is supplied to the $k^{th}$ display write line GWLk. Therefore, the sensing signal transistor SRT may be turned off during the first period t1 and the third period t3. Accordingly, during the first period t1 and the third period t3, the voltage of the sensing anode electrode of the photo-detecting element PD may increase by the incident light. For example, as the amount of light incident on the photo-detecting element PD increases, the voltage at the sensing anode electrode of the photo-detecting element PD may increase.

Secondly, during the second period t2, the $k^{th}$ display scan signal GWk having the first level voltage V1 is supplied to the $k^{th}$ display write line GWLk. Therefore, during the second period t2, each of the second transistor ST2, the third transistor ST3 and the sensing signal transistor SRT is turned on by the $k^{th}$ display scan signal GWk having the first level voltage V1.

During the second period t2, as the third transistor ST3 is turned on, the gate electrode and the second electrode of the driving transistor DT are connected to each other, and the driving transistor DT works as a diode. In addition, during the second period t2, as the second transistor ST2 is turned on, the data voltage Vdata is applied to the first electrode of the driving transistor DT. At this time, since the voltage between the first electrode and the gate electrode of the driving transistor DT (Vsg=Vdata−VINT) is smaller than the threshold voltage Vth, the driving transistor DT forms a current path until the voltage Vsg between the first electrode and the gate electrode reaches the threshold voltage Vth. Accordingly, the gate electrode and the second electrode of the driving transistor DT increases up to the voltage difference (Vdata−Vth) between the data voltage Vdata and the threshold voltage Vth of the driving transistor DT during the second period t2.

During the second period t2, as the sensing signal transistor SRT is turned on, the sensing anode electrode of the photo-detecting element PD may be connected to the $q^{th}$ light-sensing line RLq. Therefore, the blood-pressure detecting circuit 400 may sense the voltage at the sensing anode electrode of the photo-detecting element PD through the $q^{th}$ light-sensing line RLq.

Thirdly, the $k^{th}$ emission signal EMk having the first level voltage V1 is supplied to the $k^{th}$ emission line Ek during the third period t3. During the third period t3, each of fifth transistor ST5 and the sixth transistor ST6 is turned on by the $k^{th}$ emission signal EMk having the first level voltage V1.

As the fifth transistor ST5 is turned on, the first electrode of the driving transistor DT is connected to the first supply voltage line VDL. As the sixth transistor ST6 is turned on, the second electrode of the driving transistor DT is connected to the anode electrode of the light-emitting element LEL.

When the fifth transistor ST5 and the sixth transistor ST6 are turned on, the driving current Ids flowing can be supplied to the light-emitting element LEL according to the voltage at the gate electrode of the driving transistor DT. The driving current Ids may be defined as shown in Equation 2 below:

$$Ids = k' \times \{VDD - (Vdata - Vth) - Vth\}^2 \quad \text{[Equation 2]}$$

where k' denotes a proportional coefficient determined by the structure and physical properties of the driving transistor DT, Vth denotes the threshold voltage of the driving transistor DT, VDD denotes the first supply voltage from the first supply voltage line VDL, and Vdata denotes the data voltage. The voltage at the gate electrode of the driving transistor DT is equal to Vdata−Vth, and the voltage at the first electrode is equal to VDD. Equation 3, as shown below, may be derived from Equation 2.

$$Ids = k' \times (VDD - Vdata)^2 \quad \text{[Equation 3]}$$

Consequently, the driving current Ids does not depend on the threshold voltage Vth of the driving transistor DT as in Equation 3. For example, the threshold voltage Vth of the driving transistor DT can be compensated.

Figure 10:
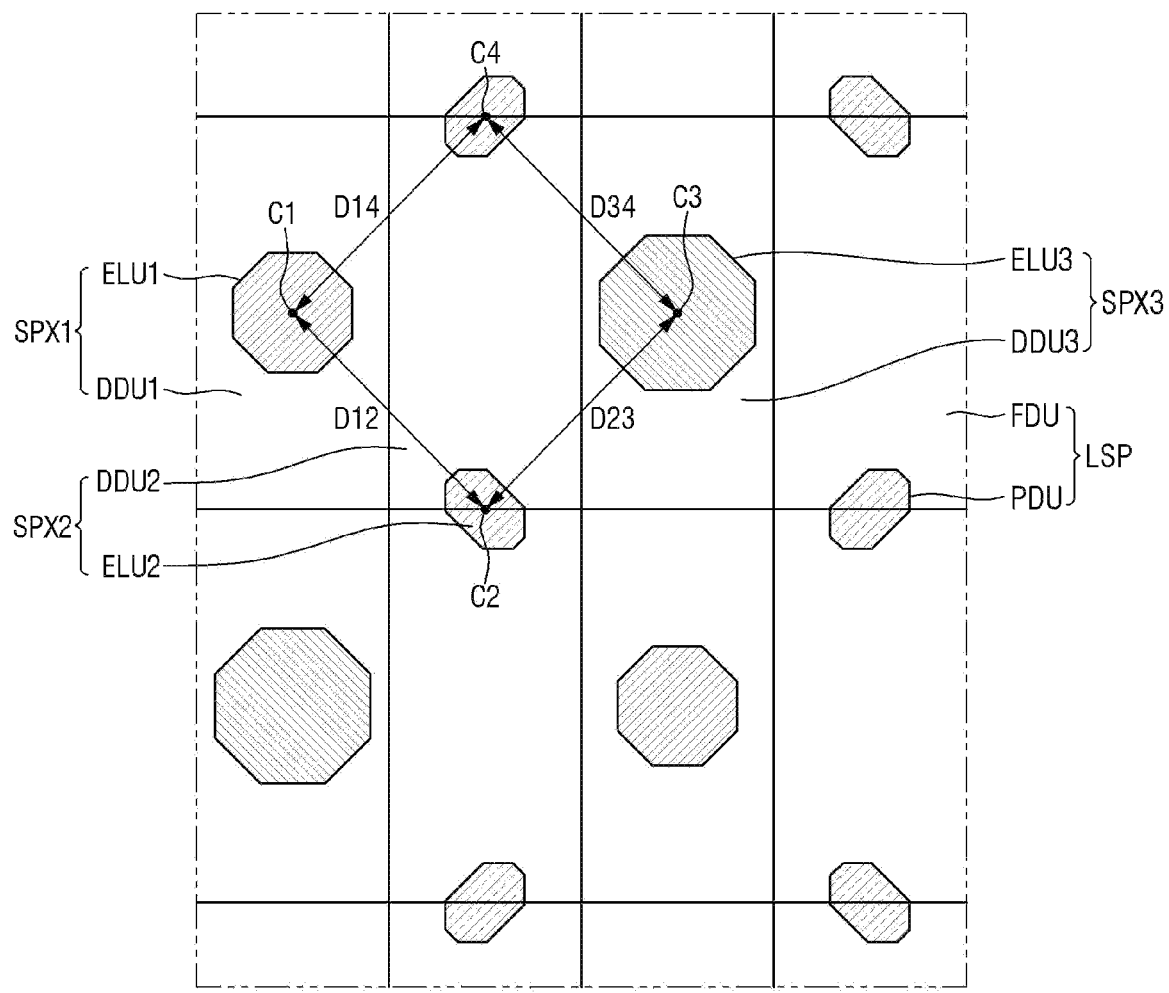
FIG. 10 is a layout view of a display area according to an embodiment of the present disclosure.

FIG. 10 is a layout view of a display area according to an embodiment of the present disclosure.

Referring to FIG. 10, the display area DA may include first display pixels SPX1, second display pixels SPX2, third display pixels SPX3, and light-sensing pixels LSP. For example, the display pixels SPX may be divided into first display pixels SPX1, second display pixels SPX2 and third display pixels SPX3. The light-sensing pixels LSP including the first display pixel SPX1, the second display pixel SPX2 and the third display pixel SPX3 may be defined as a unit display pixel USPX. The unit display pixel USPX may be defined as the minimum unit of display pixels capable of representing white and sensing light.

The first display pixel SPX1 may include a first light-emitting unit ELU1 that emits first light and a first pixel driving unit DDU1 that applies a driving current to the light-emitting element of the first light-emitting unit ELUL. The first light may be light in a red wavelength range. For example, the main peak wavelength of the first light may be located between about 600 nm and about 750 nm.

The second display pixel SPX2 may include a second light-emitting unit ELU2 that emits second light and a second pixel driving unit DDU2 that applies a driving current to the light-emitting element of the second light-emitting unit ELU2. The second light may be light in a green wavelength range. For example, the main peak wavelength of the second light may be located between about 480 nm and about 560 nm.

The third display pixel SPX3 may include a third light-emitting unit ELU3 that emits third light and a third pixel driving unit DDU3 that applies a driving current to the light-emitting element of the third light-emitting unit ELU3. The third light may be light in a blue wavelength range. For example, the main peak wavelength of the third light may be located between about 370 nm and about 460 nm.

The light-sensing pixel LSP may include a photo-detecting unit PDU and a sensing driving unit FDU.

In a unit display pixel USPX, the first to third pixel driving units DDU1 to DDU3 and the sensing driving unit FDU may be sequentially arranged in the first direction DR1. All of the first pixel driving units DDU1 adjacent to one another in the data line direction may be arranged in the second direction DR2. All of the second pixel driving units DDU2 adjacent to one another in the data line direction may be arranged in the second direction DR2. Similarly, all of the sensing driving units FDU adjacent to one another in the data line direction may be arranged in the second direction DR2.

The first light-emitting unit ELU1 may overlap the first pixel driving unit DDU1, and the third light-emitting unit ELU3 may overlap the third pixel driving unit DDU3. The second light-emitting unit ELU2 and the photo-detecting unit PDU may overlap the second pixel driving unit DDU2 and the sensing driving unit FDU, respectively. The second light-emitting unit ELU2 and the photo-detecting unit PDU may be disposed at the borders of the second pixel driving unit DDU2 and the sensing driving unit FDU, respectively.

The first light-emitting unit ELU1, the second light-emitting unit ELU2, the third light-emitting unit ELU3 and the photo-detecting unit PDU may have, but is not limited to, an octagonal shape when viewed from the top (e.g., when viewed in a plan view). The first light-emitting unit ELU1, the second light-emitting unit ELU2, the third light-emitting unit ELU3 and the photo-detecting unit PDU may have a quadrangular shape such as, for example, a diamond, or a polygonal shape other than a square and an octagon when viewed from the top.

Due to the arrangement positions and planar shapes of the first light-emitting unit ELU1, the second light-emitting unit ELU2, the third light-emitting unit ELU3 and the photo-detecting unit PDU, the distance D12 between the center C1 of the first light-emitting unit ELU1 and the center C2 of the second light-emitting unit ELU2, the distance D23 between the center C2 of the second light-emitting unit ELU2 and the center C3 of the third light-emitting unit ELU3, the distance D14 between the center C1 of the first light-emitting unit ELU1 and the center C4 of the second light-emitting unit ELU2, and the distance D34 between the center C4 of the second light-emitting unit ELU2 and the center C3 of the third light-emitting unit ELU3 may be substantially equal to one another.

Figure 11:
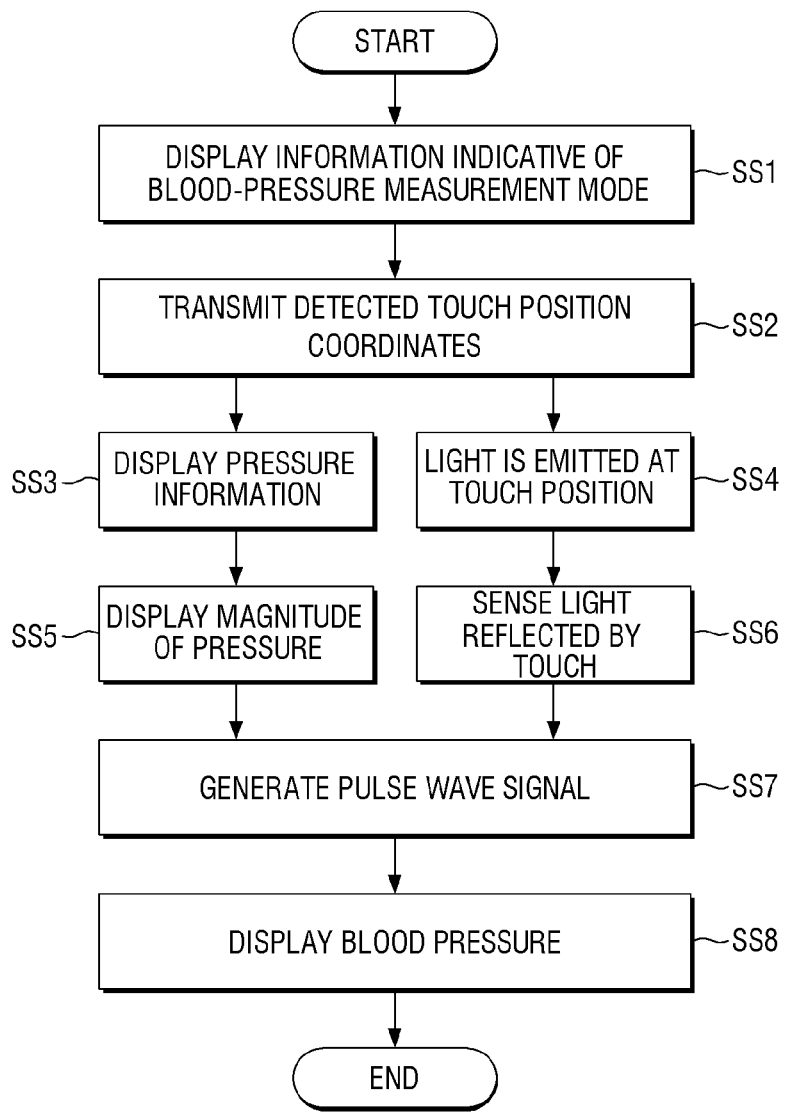
FIG. 11 is a flowchart illustrating a method of measuring blood pressure by a display device according to an embodiment of the present disclosure.
Figure 12:
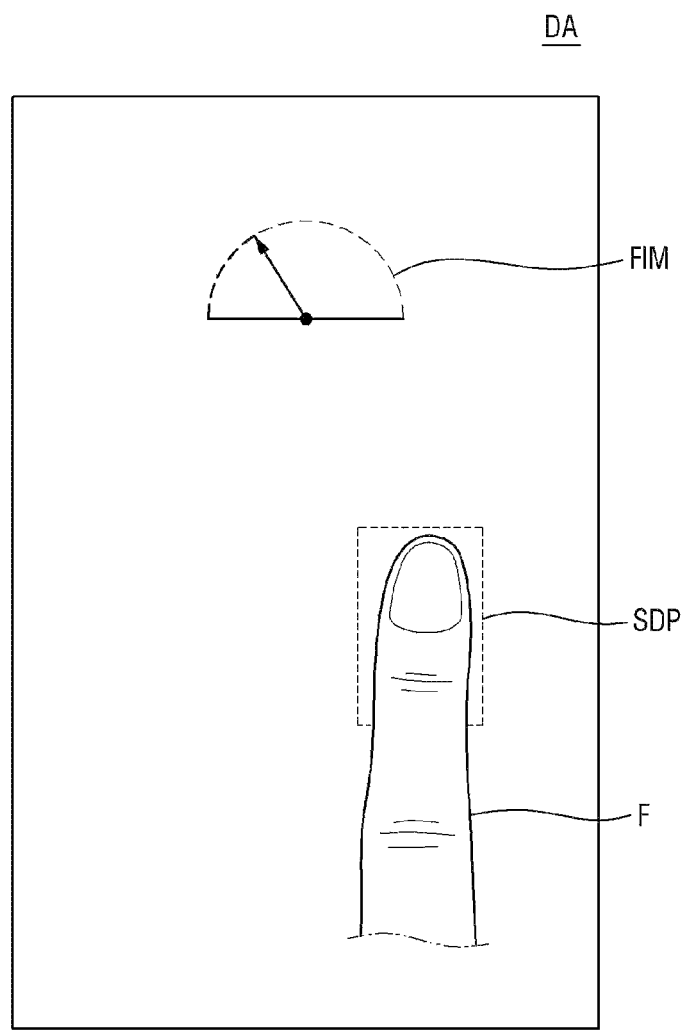
FIG. 12 is a view showing a displayed image during a blood-pressure detection period according to an embodiment of the present disclosure.

FIG. 11 is a flowchart illustrating a method of measuring blood pressure by a display device according to an embodiment of the present disclosure. FIG. 12 is a view showing a displayed image during a blood-pressure detection period according to an embodiment of the present disclosure.

Referring to FIGS. 11 and 12, the display driving circuit 200 may be switched from an image display mode, or from a power saving or standby mode, to a blood-pressure measurement mode when a user selects a blood-pressure measurement function or runs an application.

When the display driving circuit 200 is switched to the blood-pressure measurement mode, the timing controller 220 of the display driving circuit 200 controls the data driver 210 and the display scan driver 110 to display information on the display area DA indicating that the device has been switched to the blood-pressure measurement mode (operation SS1). For example, the display driving circuit 200 may display a message on the display panel 100 such as, for example, a message prompting a user to touch the device with a part of the body such as a finger to the device upon being switched to the blood-pressure measurement mode.

In the blood-pressure measurement mode, the touch driver 500 receives touch sensing signals in real time through the touch sensing unit TSU of the display panel 100 to detect touch data and touch coordinate data. The touch driver 500 transmits the touch data and the touch coordinate data detected in real time to the timing controller 220 (operation SS2).

Referring to FIGS. 11 and 12, in an embodiment, the timing controller 220 allows a predetermined pressure information display image FIM to be displayed on the display area DA via an option, and receives and displays pressure data in real time to show a change in the magnitude of the pressure applied by the user as the pressure information display image FIM (operation SS3).

The timing controller 220 detects and sets a body part touch area SDP, corresponding to a body part such as the finger F, based on the touch data and the touch coordinate data. Then, the timing controller 220 controls the data driver 210 and the display scan driver 110 so that the display pixels SPX of the body part touch area SDP emit light with a predetermined brightness (operation SS4). To this end, the timing controller 220 may arrange predetermined grayscale data for sensing blood pressure according to the location of the body part touch area SDP to supply the grayscale data to the data driver 210. Then, the timing controller 220 controls the driving timing of the data driver 210 and the display scan driver 110 so that the display pixels SPX of the body part touch area SDP emit light. Subsequently, the timing controller 220 supplies the coordinate information on the body part touch area SDP to the blood-pressure detecting circuit 400.

The touch driver 500 receives pressure sensing signals in real time through the pressure sensing unit PSU of the display panel 100, and generates pressure data according to a change in the magnitude of the pressure through the pressure sensing signals to transmit the pressure data to the timing controller 220. Accordingly, the timing controller 220 may convert a change in pressure according to the pressure data into a pressure information display image FIM in real time to display the pressure information (operation SS5).

Incidentally, the light emitted from the display pixels SPX arranged in the body part touch area SDP is reflected from the user's body part such as the finger F, and may be sensed by the photo-detecting unit PDU of the light-sensing pixel LSP (operation SS6).

The sensing driving unit FDU of the light-sensing pixel LSP outputs light-sensing signals to the light-sensing lines RL in response to the $(k-3)^{th}$ display scan signals GW(k−3). Accordingly, the blood-pressure detecting circuit 400 receives the light-sensing signals from the light-sensing lines RL associated with the body part touch area SDP based on the coordinate information of the body part touch area SDP input from the timing controller 22. Then, the blood-pressure detecting circuit 400 converts the received light-sensing signals into digital data signals.

Figure 13:
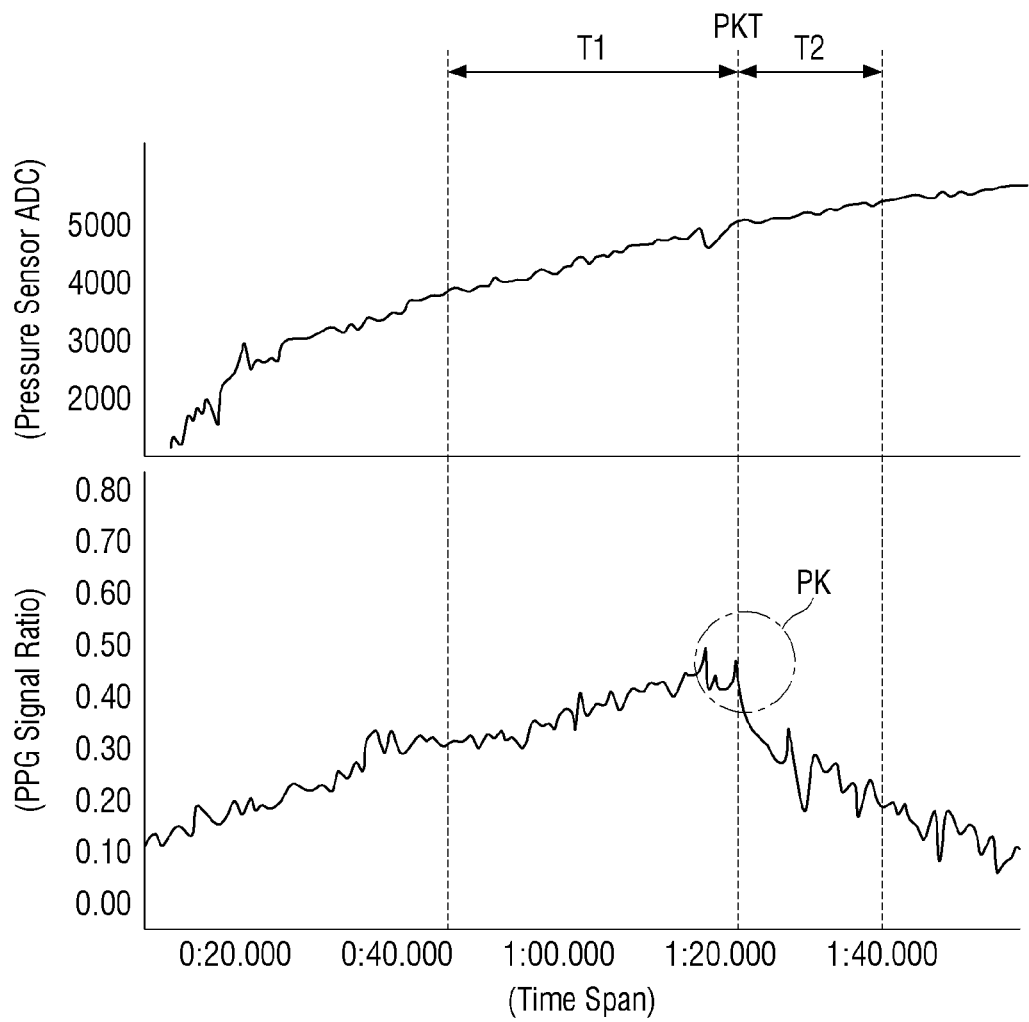
FIG. 13 is a pair of graphs illustrating a method of calculating blood pressure by a blood-pressure detecting circuit according to an embodiment of the present disclosure.

FIG. 13 is a pair of graphs illustrating a method of calculating blood pressure by a blood-pressure detecting circuit according to an embodiment of the present disclosure.

Referring to FIG. 13, the blood ejected from the left ventricle of a heart (e.g., a systole of a heart) moves to the peripheral tissues, and accordingly the blood volume in the artery increases. In addition, red blood cells carry more oxygen in hemoglobin to the peripheral tissues during the systole of the heart. During a diastole of the heart, a part of the blood is sucked from the peripheral tissues towards the heart. When a peripheral blood vessel is irradiated with light, the irradiated light is absorbed by the peripheral tissue. The light absorbance is dependent on the hematocrit ratio and the blood volume. The light absorbance may have the maximum value in the systole of the heart and the minimum value in the diastole of the heart. The light absorbance may have the maximum value in the systole of the heart and the minimum value in the diastole of the heart.

In addition, when the user touches the display panel 100 with her/his finger F in the blood-pressure measurement mode and then takes it off, the pressure (contact pressure) applied to the pressure sensing unit PSU may gradually increase to reach the maximum value and then may gradually decrease. As the contact pressure increases, the blood vessels may constrict, resulting in small or zero blood flow rate. When the contact pressure decreases, the blood vessels dilate and blood begins to flow again. When the contact pressure further decreases, the blood flow rate increases more. Therefore, a change in the amount of light sensed by the photo-detecting element PD may be proportional to a change in blood flow. Accordingly, the blood-pressure detecting circuit 400 generates a pulse wave signal according to the pressure applied by the user based on the pressure data value that is calculated by the pressure sensing unit PSU and that is digitally converted (e.g., by an ADC of the pressure sensing unit) and the optical signal (PPG signal ratio) according to the amount of light detected by the photo-detecting element PD (operation SS7 in FIG. 11). The pulse wave signal may have a waveform that oscillates according to a heartbeat cycle.

The blood-pressure detecting circuit 400 may estimate blood pressures of the blood vessels of the finger F based on time differences between time points PKT corresponding to the peaks PK of the calculated pulse wave signal and time points corresponding to the peaks of the filtered pulse wave signal. For example, the blood-pressure detecting circuit 400 may calculate pulse wave signals for predetermined time periods T1 and T2 before and after the time points PKT corresponding to the peaks PK of the calculated pulse wave signal and may detect the blood pressure according to differences between the pulse wave signals. Among the estimated blood pressures, the blood pressure having the maximum magnitude may be calculated as the systolic blood pressure, and the blood pressure having the minimum magnitude may be calculated as the diastolic blood pressure. In addition, other blood pressures such as the average blood pressure may be calculated using the estimated blood pressures. The timing controller 220 displays the detected blood pressure information on the display area DA (operation SS8 in FIG. 11).

The above-described method for measuring blood pressure is merely illustrative. It is to be understood that a variety of methods may be employed such as, for example, methods disclosed in Korean Patent Laid-Open Publication Nos. 10-2018-0076050, 10-2017-0049280 and 10-2019-0040527, the entire contents of which are incorporated by reference herein in their entireties.

Figure 14:
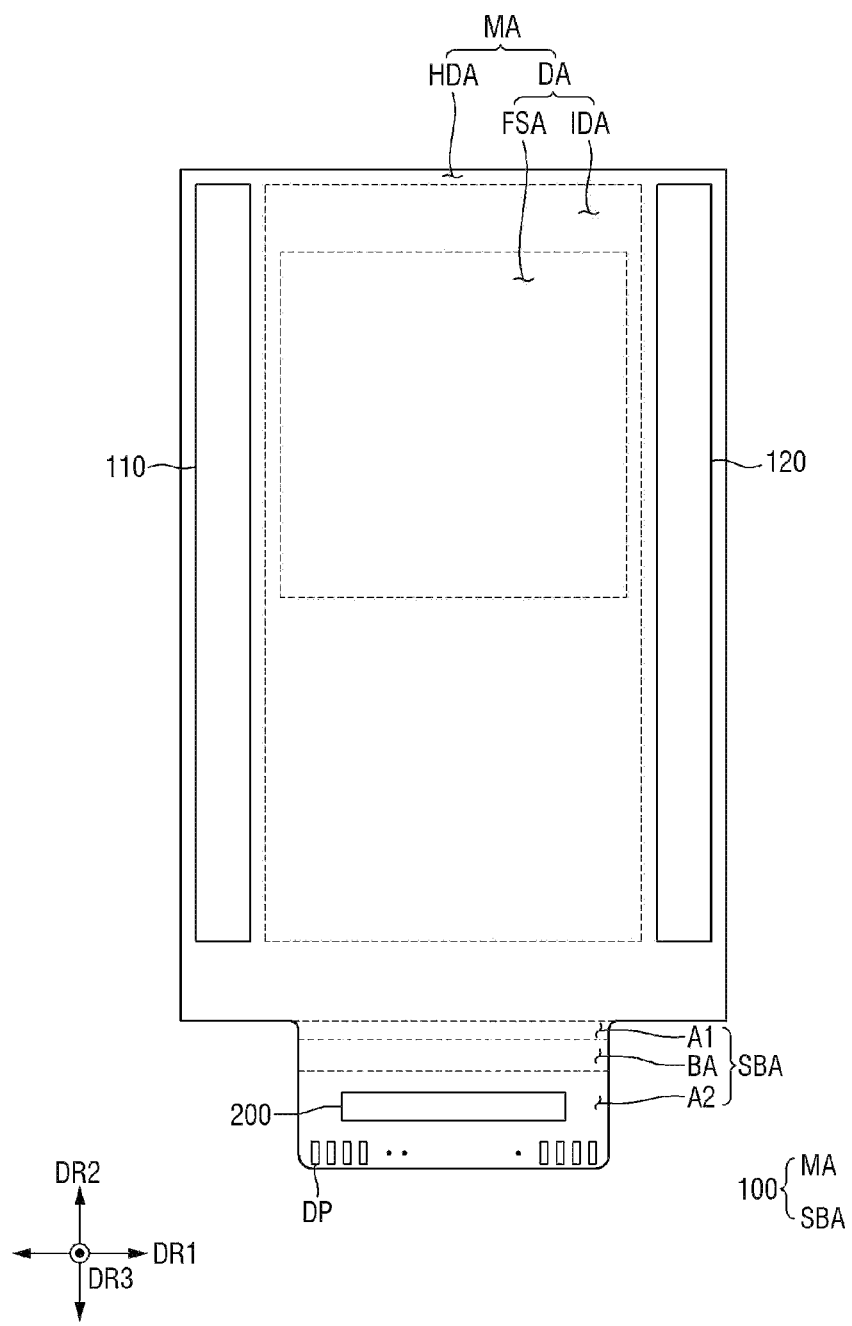
FIG. 14 is a plan view showing the arrangement structure of the display panel and the display driving circuit according to an embodiment of the present disclosure.

FIG. 14 is a plan view showing the arrangement structure of the display panel and the display driving circuit according to an embodiment of the present disclosure.

Referring to FIG. 14, in an embodiment, the display area DA may be divided into an image display area IDA in which only display pixels are disposed without light-sensing pixels, and a blood-pressure detection area FSA in which the display pixels SPX as well as the light-sensing pixels LSP are disposed. For example, the light-sensing pixels LSP may be disposed together with the display pixels SPX only in a predetermined part of the entire display area DA of the display panel 100, e.g., in the blood-pressure detection area FSA. In the following description, it is assumed that the display pixels SPX and the light-sensing pixels LSP are alternately arranged in the entire display area DA.

Figure 15:
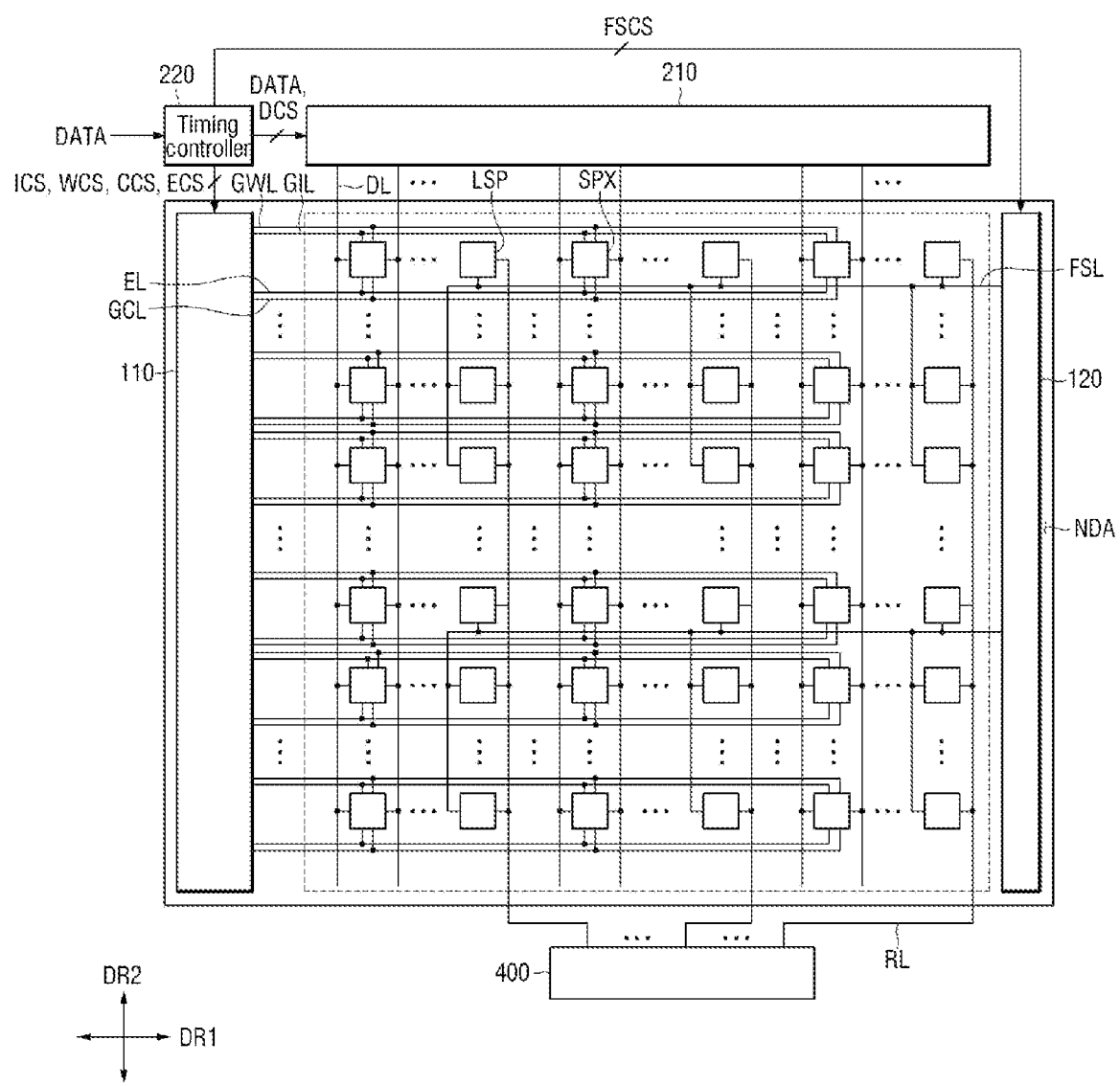
FIG. 15 is a block diagram showing in detail a display device according to an embodiment of the present disclosure.

FIG. 15 is a block diagram showing in detail a display device according to an embodiment of the present disclosure.

Referring to FIGS. 14 and 15, a display device according to an embodiment may further include a light-sensing driver 120 that supplies a sensing scan signal to the light-sensing pixels LSP separately from a display scan driver 110.

In the display panel 100 including the display area DA, the light-sensing scan lines FSL may be further included, which are horizontally disposed on the same line as the display write lines GWL and apply the sensing scan signals from the light-sensing driver 120 to the light-sensing pixels LSP.

The light-sensing driver 120 may be disposed in the non-display area NDA. Although the light-sensing driver 120 is disposed on the opposite side (e.g., the right side) of the display panel 100 in FIGS. 14 and 15, embodiments of the present disclosure are not limited thereto.

The light-sensing driver 120 may be electrically connected to the display driving circuit 200 through fan-out lines in the non-display area NDA. The light-sensing driver 120 may receive a light-sensing control signal FSCS from the display driving circuit 200 and may generate sensing scan signals predetermined at least every horizontal period according to the light-sensing control signal FSCS. The light-sensing driver 120 supplies sensing scan signals to the light-sensing pixels LSP through the light-sensing scan lines FSL. Accordingly, the light-sensing pixels LSP transmit a light-sensing signal according to the results of detecting the amount of light to the respective light-sensing lines RL in response to the sensing scan signals sequentially applied from the light-sensing driver 120.

Figure 16:
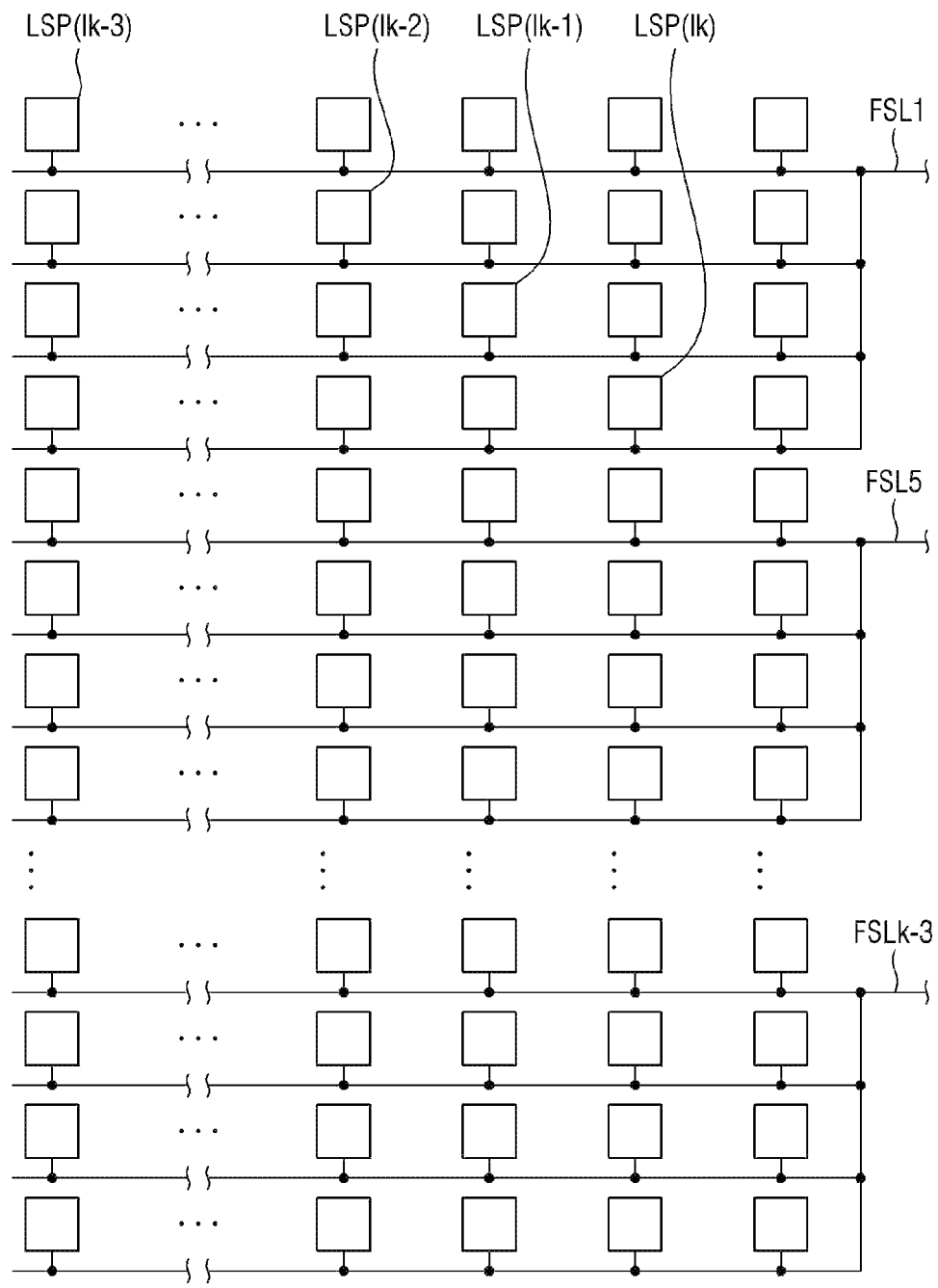
FIG. 16 is a diagram showing a connection structure of light-sensing scan lines and light-sensing pixels of the display panel shown in FIG. 15 according to an embodiment of the present disclosure.

FIG. 16 is a diagram showing a connection structure of light-sensing scan lines and light-sensing pixels of the display panel shown in FIG. 15 according to an embodiment of the present disclosure.

Referring to FIG. 16, among the light-sensing scan lines FSL connected to apply the sensing scan signals to the light-sensing pixels LSP of the display area DA, the $(k-3)^{th}$ light-sensing scan lines FSL1, FSL5, . . . FSL(k-3) may be electrically connected to the light-sensing pixels LSP(lk-3) to LSPlk disposed proximate to the $(k-3)^{th}$ to $k^{th}$ horizontal lines arranged adjacent to one another. The light-sensing scan lines FSL may each be divided into at least two horizontal lines disposed adjacent to each other and connected to the light-sensing pixels LSP disposed proximate to the at least two horizontal lines (e.g., the light-sensing pixels LSP corresponding to the at least two horizontal lines). For example, in an embodiment according to FIG. 16, each of the illustrated light-sensing scan lines FSL1, FSL5 and FSLk-3 is respectively divided into 4 horizontal lines, and each of these 4 horizontal lines is connected to light-sensing pixels LSP disposed proximate to the respective horizontal lines. For example, in an embodiment, each of the 4 horizontal lines is connected to light-sensing pixels LSP disposed in a row closest to the respective horizontal line.

For example, among the light-sensing scan lines FSL, each of the $(k-3)^{th}$ light-sensing scan lines FSL1, FSL5, . . . FSL(k-3) may extend or branch into the $(k-2)^{th}$, the $(k-1)^{th}$ and $k^{th}$ light-sensing scan lines FSL(k-2), FSL(k-1) and FSLk.

The light-sensing pixels LSP arranged side by side in each horizontal line receive display scan signals through one of the light-sensing scan lines FSL. For example, the light-sensing pixels LSP(lk-3) to LSP(lk) in the $(k-3)^{th}$ to $k^{th}$ horizontal lines may be connected to one of the $(k-3)^{th}$ light-sensing scan lines FSL1, FSL5, . . . FSL(k-3). Accordingly, the light-sensing pixels LSP(lk-3) to LSP(lk) arranged in the $(k-3)^{th}$ to $k^{th}$ horizontal lines transmit the light-sensing signal according to the amount of reflected light on the front surface to the respective light-sensing lines RL in response to the $(k-3)^{th}$ sensing scan signal supplied through the $(k-3)^{th}$ light-sensing scan line FSL1, FSL5, . . . FSL(k-3).

Figure 17:
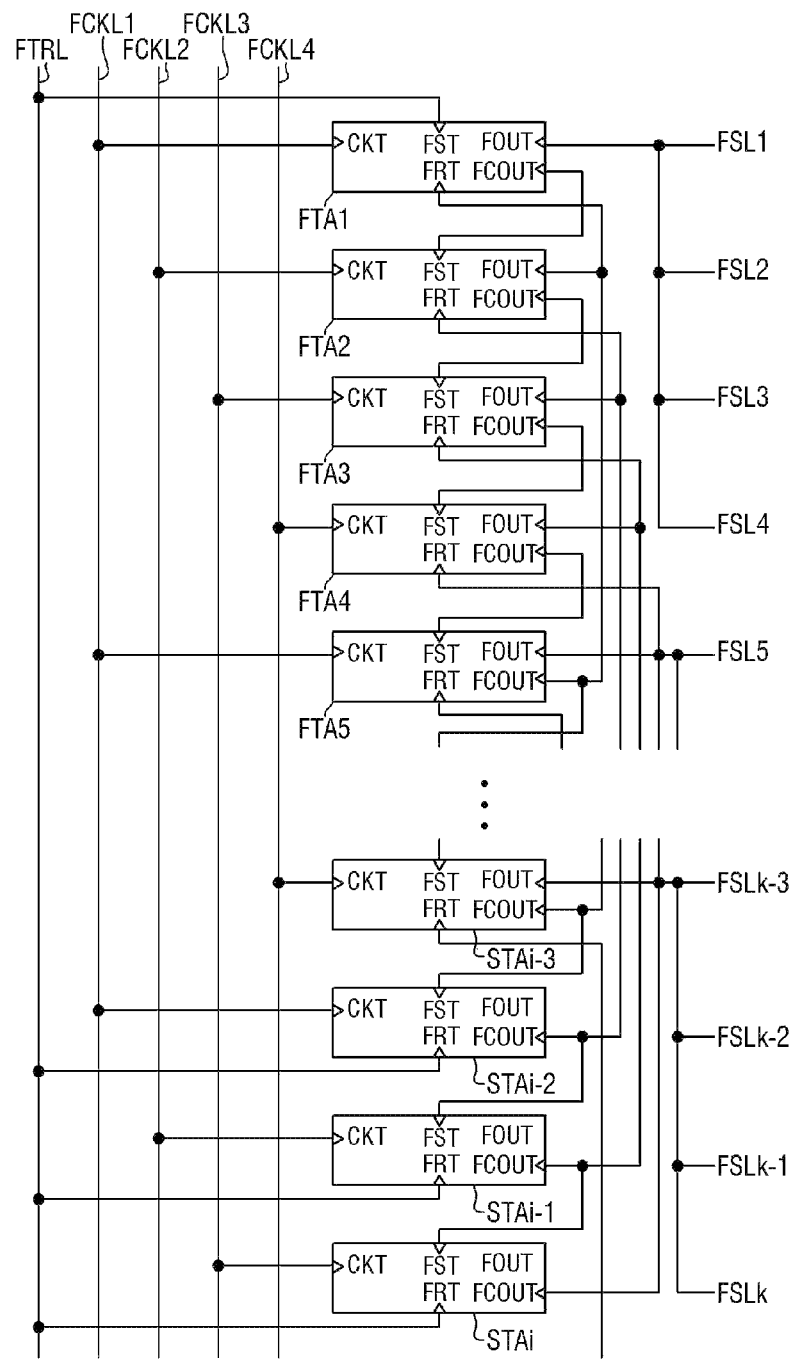
FIG. 17 is a view showing an example of the light-sensing driver according to an embodiment of the present disclosure.

FIG. 17 is a view showing an example of the light-sensing driver according to an embodiment of the present disclosure.

Referring to FIG. 17, the light-sensing driver 120 may include a plurality of sensing stages FTA1, FTA2, FTA3, FTA4, . . . , FTA(i-1) and FTAi, where i is an integer less than m and i and m are positive integers. Each of the plurality of sensing stages FTA1, FTA2, FTA3, FTA4, . . . , FTA(i-1) and FTAi may include a sensing start signal input FST, a sensing reset signal input FRT, a sensing clock signal input FCKT, a sensing scan signal output FOUT and a sensing carry signal output FCOUT.

The sensing start signal input FST of each of the plurality of sensing stages FTA1, FTA2, FTA3, FTA4, . . . , FTA(i-1) and FTAi may be connected to a sensing start line FTRL or the sensing carry signal output FCOUT of the previous sensing stage. For example, the start signal input ST of the first sensing stage FTA1 may be connected to the sensing start line FTRL from which the sensing start signal is input. In addition, the sensing start signal input FST of each of the plurality of sensing stages FTA2, FTA3, FTA4, . . . , FTA(i-1) and FTAi except the first sensing stage FTA1 may be connected to the sensing carry signal output FCOUT of the previous sensing stage. For example, the sensing start signal input FST of the second sensing stage FTA2 may be connected to the sensing carry signal output FCOUT of the first sensing stage FTA1, and the sensing start signal input FST of the third sensing stage FTA3 may be connected to the sensing carry signal output FOUT of the second sensing stage FTA2.

The sensing reset signal input FRT of each of the plurality of sensing stages FTA1, FTA2, FTA3, FTA4, . . . , FTA(i-1) and FTAi may be connected to the sensing carry signal output FCOUT of the subsequent sensing stage. For example, the sensing reset signal input FRT of the first sensing stage FTA1 may be connected to the sensing carry signal output FCOUT of the fifth sensing stage FTA5.

The sensing clock signal input FCKT of each of the plurality of sensing stages FTA1, FTA2, FTA3, FTA4, . . . , FTA(i-1) and FTAi may be connected to one of the sensing clock lines FCKL1, FCKL2, FCKL3 and FCKL4.

The plurality of sensing stages FTA1, FTA2, FTA3, FTA4, . . . , FTA(i-1) and FTAi may be sequentially connected to the sensing clock lines FCKL1, FCKL2, FCKL3 and FCKL4. For example, the sensing clock signal input FCKT of the first sensing stage FTA1 may be connected to the first sensing clock line FCKL1, and the sensing clock signal input FCKT of the second sensing stage FTA2 may be connected to the second sensing clock line FCKL2. The sensing clock signal input FCKT of the third sensing stage FTA3 may be connected to the third sensing clock line FCKL3, and the sensing clock signal input FCKT of the fourth sensing stage FTA4 may be connected to the fourth sensing clock line FCKL4.

The plurality of sensing stages FTA1, FTA2, FTA3, FTA4, . . . , FTA(i-1) and FTAi may be connected to the light-sensing scan lines FSL1, FSL2, FSL3, FSL4, . . . , FSL(i-1) and FSLi. The display scan signal output FOUT of each of the plurality of sensing stages FTA1, FTA2, FTA3, FTA4, . . . , FTA(i-1) and FTAi may be connected to the respective light-sensing scan line FSL. For example, the first sensing stage FTA1 may be connected to the first light-sensing scan line FSL1, and the second sensing stage FTA2 may be connected to the second light-sensing scan line FSL2. In addition, the third sensing stage FTA3 may be connected to the third light-sensing scan line FSL3, and the fourth sensing stage FTA4 may be connected to the fourth light-sensing scan line FSL4. In addition, the $(i-1)^{th}$ sensing stage FTA(i-1) may be connected to the $(i-1)^{th}$ light-sensing scan line FSL(i-1), and the ith sensing stage FTAi may be connected to the ith light-sensing scan line FSLi.

The sensing carry signal output COUT of each of the plurality of sensing stages FTA1, FTA2, FTA3, FTA4, . . . , FTA(i-1) and FTAi may be connected to the sensing reset signal input RT of the previous sensing stage and the sensing start signal input ST of the subsequent sensing stage. According to an embodiment, the carry signal output COUT of each of the first sensing stage FTA1, the second sensing stage FTA2, the third sensing stage FTA3 and the fourth sensing stage fTA4 may be connected only to the start signal input ST of the subsequent sensing stage.

The plurality of sensing stages FTA1, FTA2, FTA3, FTA4, . . . , FTA(i-1) and FTAi may provide sensing scan signals to the sensing driving unit FDU connected to the photo-detecting units PDU of the display area DA. As described above, the $(k-3)^{th}$ display write lines GWL1, GWL5, . . . GWL(k-3) may be electrically connected to the light-sensing pixels LSP(lk-3) to LSP(lk) arranged adjacent to one another. Accordingly, each of the $(k-3)^{th}$ display write lines GWL1, GWL5, . . . GWL(k-3) may extend or branch into the $(k-2)^{th}$, $(k-1)^{th}$ and $k^{th}$ display write lines GWL(k-2), GWL(k-1) and GWL(k-1).

Figure 18:
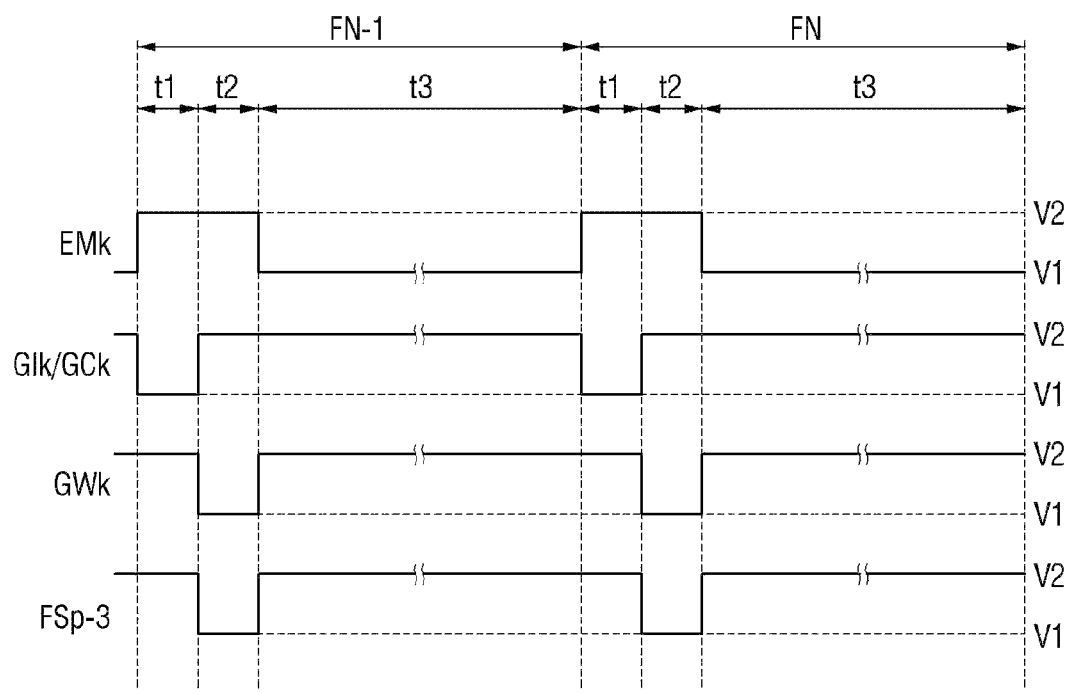
FIG. 18 is a waveform diagram showing scan signals input to a display pixel and a light-sensing pixel according to an embodiment of the present disclosure.

FIG. 18 is a waveform diagram showing scan signals input to a display pixel and a light-sensing pixel according to an embodiment of the present disclosure.

In FIG. 18, the $k^{th}$ display emission signal Emk applied to the $k^{th}$ display emission line Elk, the $k^{th}$ display initialization signal GIk applied to the $k^{th}$ display initialization line GILk, the $k^{th}$ display control signal GCk applied to the $k^{th}$ display control line GCLk, the $k^{th}$ display scan signal GWk applied to the $k^{th}$ display write line GWLk, and the sensing scan signal FSp-3 applied to the $(k-3)^{th}$ display write lines GWL1, GWL5, . . . GWL(k-3) during the $(n-1)^{th}$ frame period FN-1 and the nth frame period FN are shown.

Each of the $(n-1)^{th}$ frame period FN-1 and the nth frame period FN may include a first period t1, a second period t2, and a third period t3. During the first period t1, the gate electrode of the driving transistor DT is initialized to the third supply voltage VINT. During the second period t2, the data voltage is supplied to the gate electrode of the driving transistor DT, and the threshold voltage of the driving transistor DT is sampled. During the third period t3, the light-emitting element LEL emits light according to the gate voltage of the driving transistor DT. In addition, during the first period t1 and the third period t3, the photo-sensing element PD is exposed to light, and during the second period t2, the anode voltage of the photo-sensing element PD is sensed.

The sensing scan signals FSp-3 applied to the $(k-3)^{th}$ display write lines GWL1, GWL5, . . . GWL(k-3) have the first level voltage V1 during the first period t1, and have the second level voltage V2 during the second period t2 and the third period t3. The sensing scan signals FSp-3 may be generated and applied at the same timing as the $k^{th}$ display scan signal GWk or the $(k-3)^{th}$ display scan signal GW(k-3).

Hereinafter, operations of the display pixel SPX and the light-sensing pixel LSP during the first period t1, the second period t2 and the third period t3 will be described with reference to FIGS. 6 and 18.

In the first period t1, the $k^{th}$ display initialization signal Gik having the first level voltage V1 is supplied to the $k^{th}$ display initialization line GILk, and the $k^{th}$ display control signal GCk having the first level voltage V1 is supplied to the $k^{th}$ display control wiring GCLk. As the first transistor ST1 is turned on, the third supply voltage VINT of the third supply voltage line VIL is applied to the gate electrode of the driving transistor DT. In addition, during the first period t1, as the fourth transistor ST4 is turned on, the anode electrode of the light-emitting element LEL may be initialized to the third supply voltage VINT of the third supply voltage line VIL.

Incidentally, during the first period t1, the $(k-3)^{th}$ sensing scan signal FSp-3 having the second level voltage V2 is supplied to the $(k-3)^{th}$ display write lines GWL1, GWL5, . . . GWL(k-3). Therefore, the sensing signal transistor SRT may be turned off during the first period t1 and the third period t3. Accordingly, during the first period t1, the voltage of the sensing anode electrode of the photo-sensing element PD may increase by the incident light.

During the second period t2, as the third transistor ST3 is turned on, the gate electrode and the second electrode of the driving transistor DT are connected to each other, and the driving transistor DT works as a diode. For example, during the second period t2, the $(k-3)^{th}$ sensing scan signal FSp-3 having the first level voltage V1 is supplied to the $(k-3)^{th}$ display write lines GWL1, GWL5, . . . GWL(k-3). Therefore, during the second period t2, each of the second transistor ST2, the third transistor ST3 and the sensing signal transistor SRT is turned on by the $k^{th}$ display scan signal GWk and the $(k-3)^{th}$ sensing scan signal FSp-3 having the first level voltage V1.

During the second period t2, as the sensing signal transistor SRT is turned on, the sensing anode electrode of the photo-sensing element PD may be connected to the $q^1$ light-sensing line RLq. Therefore, the blood-pressure detecting circuit 400 may sense the voltage at the sensing anode electrode of the photo-sensing element PD through the $q^1$ light-sensing line RLq.

During the third period t3, as the sensing signal transistor SRT is turned on, the voltage at the anode electrode of the photo-detecting element PD may increase according to the incident light. For example, as the amount of light incident on the photo-detecting element PD increases, the voltage at the sensing anode electrode of the photo-detecting element PD may increase.

Figure 19:
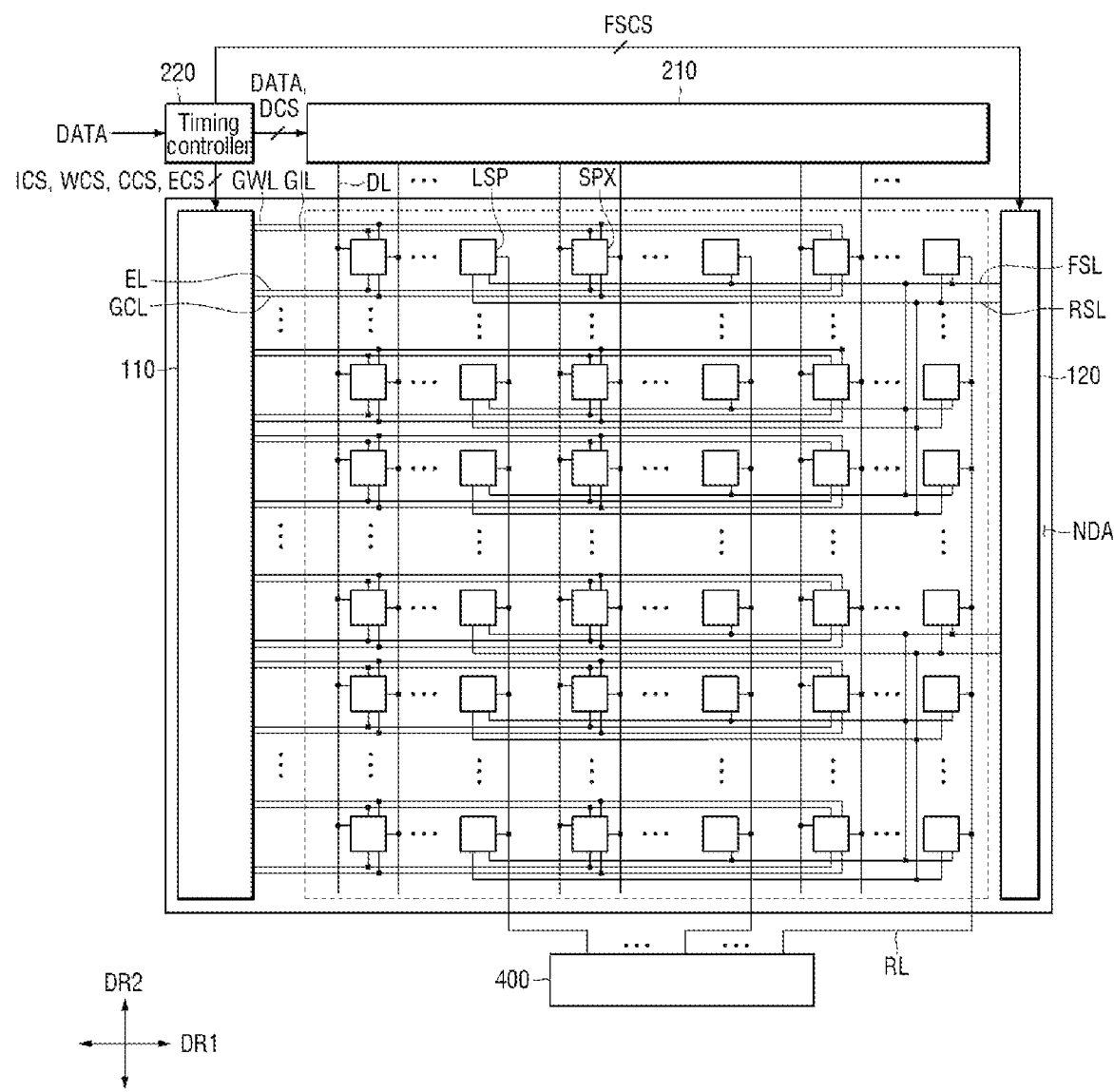
FIG. 19 is a block diagram showing in detail a display device according to an embodiment of the present disclosure.

FIG. 19 is a block diagram showing in detail a display device according to an embodiment of the present disclosure.

Referring to FIG. 19, a display device according to an embodiment may include a light-sensing driver 120 that supplies a sensing scan signal and a sensing reset signal to the light-sensing pixels LSP separately from a display scan driver 110.

In the display panel 100 including the display area DA, light-sensing scan lines FSL that apply sensing scan signals from the light-sensing driver 120 to the light-sensing pixels LSP, and sensing reset lines RSL that apply sensing reset signals from the light-sensing driver 120 to the light-sensing pixels LSP may be further included.

The light-sensing driver 120 may receive a light-sensing control signal FSCS from the display driving circuit 200 and may generate sensing scan signals and sensing reset signals predetermined at least every horizontal period according to the light-sensing control signal FSCS.

The light-sensing driver 120 supplies sensing reset signals to the light-sensing pixels LSP through the sensing reset lines RSL. Accordingly, the light-sensing pixels LSP may be temporarily reset by sensing reset signals sequentially applied from the light-sensing driver 120. In addition, the light-sensing driver 120 supplies sensing scan signals to the light-sensing pixels LSP through the light-sensing scan lines FSL. Accordingly, the light-sensing pixels LSP may transmit a light-sensing signal according to the results of detecting the amount of light to the respective light-sensing lines RL in response to the sensing scan signals sequentially applied from the light-sensing driver 120.

Figure 20:
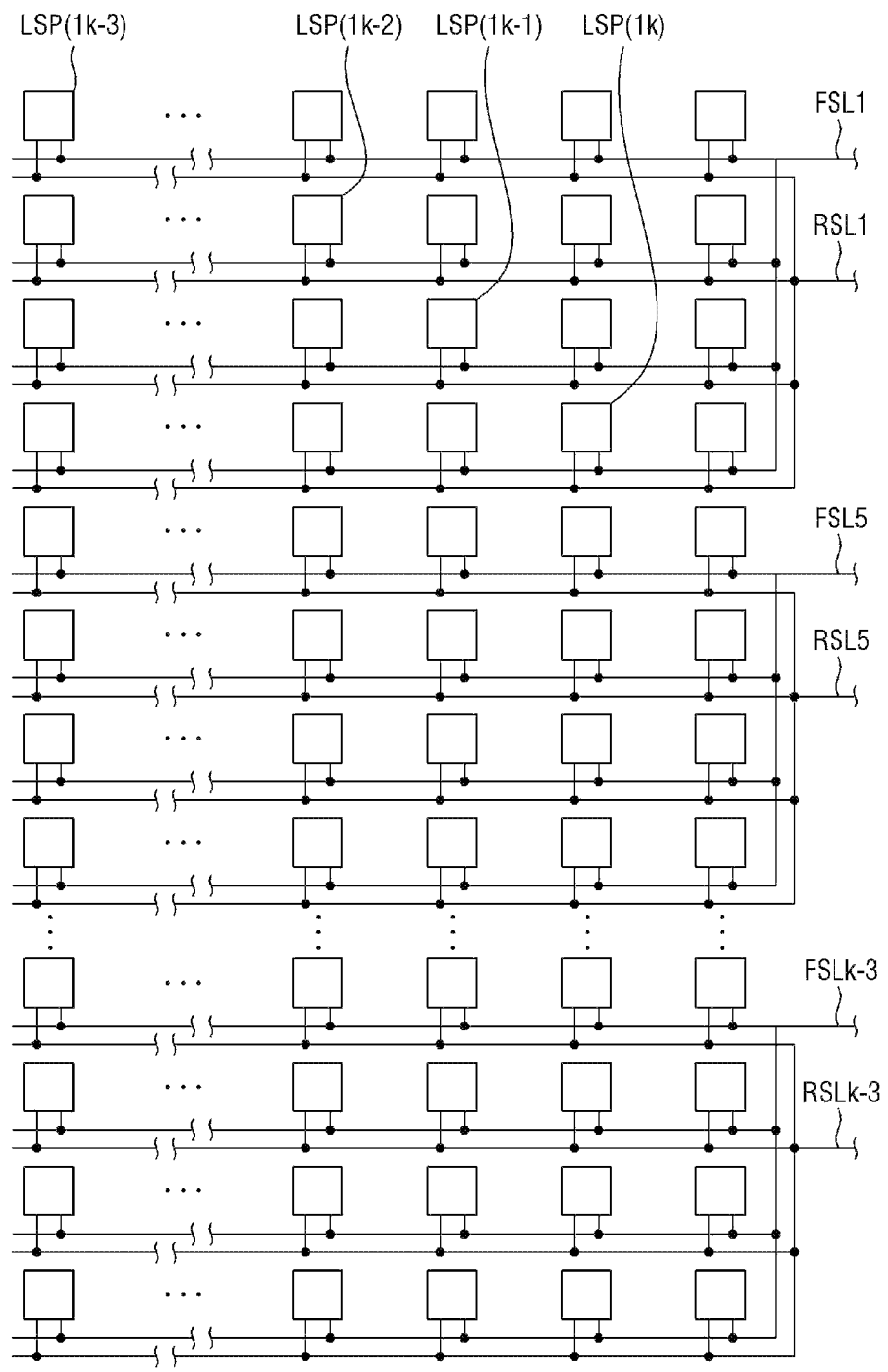
FIG. 20 is a diagram showing a connection structure of the light-sensing scan lines and the sensing reset lines connected to the light-sensing pixels shown in FIG. 19 according to an embodiment of the present disclosure.

FIG. 20 is a diagram showing a connection structure of the light-sensing scan lines and the sensing reset lines connected to the light-sensing pixels shown in FIG. 19 according to an embodiment of the present disclosure.

Referring to FIG. 20, among the light-sensing scan lines FSL, the $(k-3)^{th}$ light-sensing scan lines FSL1, FSL5, . . . FSL(k-3) may be electrically connected to the light-sensing pixels LSP(lk-3) to LSPlk of the $(k-3)^{th}$ to $k^{th}$ horizontal lines arranged adjacent to one another.

Similarly, among the sensing reset lines RSL, the $(k-3)^{th}$ sensing reset lines RSL1, RSL5, . . . RSL(k-3) may be electrically connected to the light-sensing pixels LSP(lk-3) to LSP(lk) of the $(k-3)^{th}$ to $k^{th}$ horizontal lines arranged adjacent to one another.

Among the sensing reset lines RSL, each of the $(k-3)^{th}$ sensing rest lines RSL1, RSL5, . . . RSL(k-3) may extend or branch into the $(k-2)^{th}$, the $(k-1)^{th}$ and k sensing reset lines RSL(k-2), RSL(k-1) and RSLk.

The light-sensing pixels LSP arranged side by side in each horizontal line receive sensing reset signals through one of the sensing reset lines RSL. For example, the light-sensing pixels LSP(lk-3) to LSP(lk) in the $(k-3)^{th}$ to $k^{th}$ horizontal lines may be connected to one of the $(k-3)^{th}$ sensing reset lines RSL1, RSL5, . . . RSL(k-3). Accordingly, the light-sensing pixels LSP(lk-3) to LSP(lk) in the $(k-3)^{th}$ to $k^{th}$ horizontal lines arranged adjacent to one another may be reset in response to the $(k-3)^{th}$ sensing reset signal supplied through the $(k-3)^{th}$ sensing reset lines RSL1, RSL5, . . . RSL(k-3). Subsequently, the light-sensing pixels LSP(lk-3) to LSP(lk) arranged in the $(k-3)^{th}$ to $k^{th}$ horizontal lines may transmit the light-sensing signal according to the amount of reflected light on the front surface to the respective light-sensing lines RL in response to the $(k-3)^{th}$ sensing scan signal supplied through the $(k-3)^{th}$ light-sensing scan line FSL1, FSL5, . . . FSL(k-3).

Figure 21:
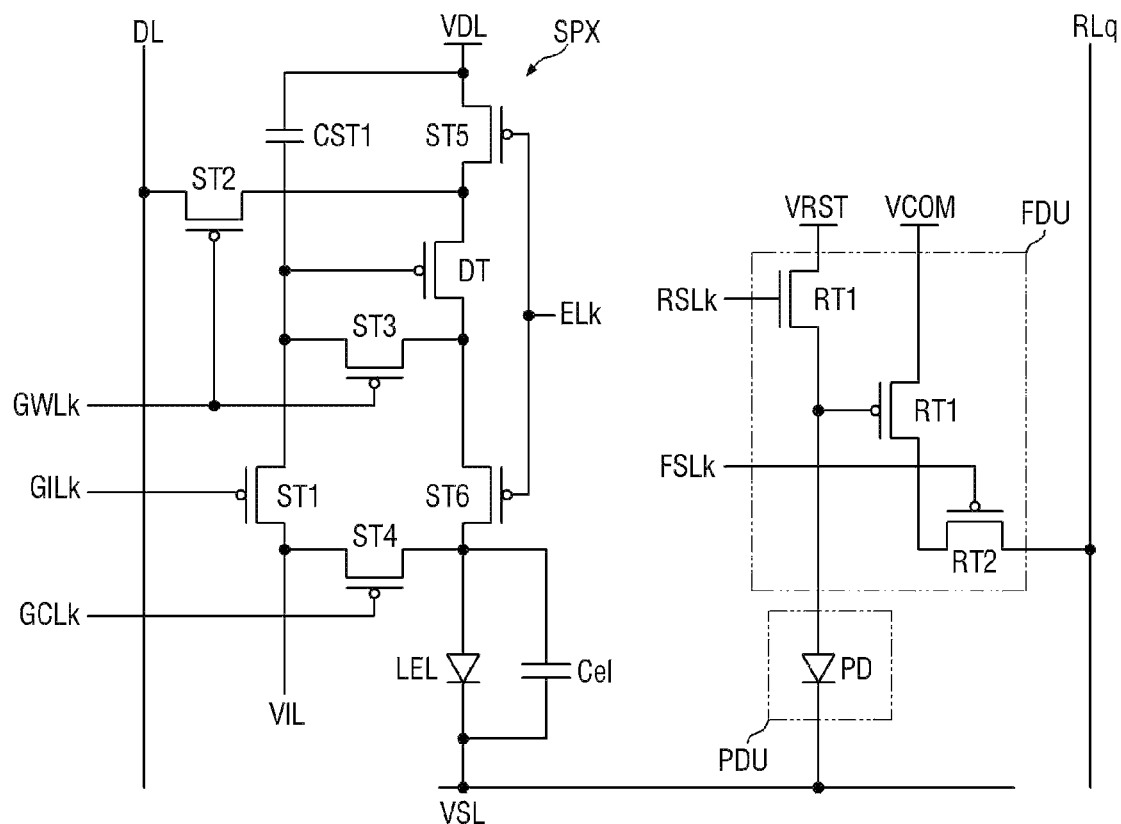
FIG. 21 is a circuit diagram showing a display pixel and a light-sensing pixel according to an embodiment of the present disclosure.

FIG. 21 is a circuit diagram showing a display pixel and a light-sensing pixel according to an embodiment of the present disclosure.

Referring to FIGS. 20 and 21, each of the display pixels SPX and the light-sensing pixels LSP arranged in the display area DA may be electrically connected to one of the sensing reset lines RSL, one of the light-sensing scan lines FSL, and one of the light-sensing lines RL. Each of the light-sensing pixels LSP may be reset by a reset signal from the sensing reset line RSL, and may transmit a light-sensing signal to each light-sensing line RL in response to the sensing scan signal from the light-sensing scan line FSL.

As shown in FIG. 21, the light-sensing pixels LSP may be divided into a photo-detecting unit PDU including a photo-detecting element PD, and a sensing driving unit FDU including first to third sensing transistors RT1 to RT3 and a sensing capacitor. The sensing capacitor may be formed in parallel with the photo-detecting element PD.

A first sensing transistor RT1 of the sensing driving unit FDU may allow a light-sensing current to flow according to the voltages of the photo-detecting element PD and the sensing capacitor. The amount of current of the light-sensing current may vary depending on a voltage applied to the photo-detecting element PD and the sensing capacitor. The gate electrode of the first sensing transistor RT1 may be connected to the second electrode of the photo-detecting element PD. A first electrode of the first sensing transistor RT1 may be connected to a common voltage source VCOM from which a common voltage is applied. A second electrode of the first sensing transistor RT1 may be connected to a first electrode of the second sensing transistor RT2.

When the sensing scan signal FSp of the gate-on voltage is applied to the light-sensing scan line FSL, the second sensing transistor RT2 allows the sensing current of the first sensing transistor RT1 to flow to the light-sensing line RLq. In this instance, the light-sensing line RLq may be charged with the sensing voltage by the sensing current. The gate electrode of the second sensing transistor RT2 may be connected to the light-sensing scan line FSL, the first electrode thereof may be connected to the second electrode of the first sensing transistor RT1, and the second electrode thereof may be connected to the light-sensing line RLq.

When a reset signal of the gate-on voltage is applied to the sensing reset line RSL, the third sensing transistor RT3 may reset the voltages of the photo-detecting element PD and the sensing capacitor to the reset voltage of a reset voltage source VRST. The gate electrode of the third sensing transistor RT3 may be connected to the sensing reset line RSL, the first electrode thereof may be connected to the reset voltage source VRST, and the second electrode thereof may be connected to the second electrode of the photo-detecting element PD.

Although the first sensing transistor RT1 and the second sensing transistor RT2 are implemented as p-type metal oxide semiconductor field effect transistors (MOSFETs) while the third sensing transistor RT3 is implemented as an n-type MOSFET in the example shown in FIG. 21, this is merely illustrative. In an embodiment, the first sensing transistor RT1 and the second sensing transistor RT2 may be of the same type or different types. In addition, one of the first and second electrodes of each of the first sensing transistor RT1, the second sensing transistor RT2 and the third sensing transistor RT3 may be a source electrode, while the other one of the first and second electrodes may be a drain electrode.

The plurality of sensing stages FTA1, FTA2, FTA3, FTA4, . . . , FTA(i-1) and FTAi included in the light-sensing driver 120 may provide the $(k-3)^{th}$ sensing scan signals and the $(k-3)^{th}$ sensing reset signals to the sensing driving unit FDU connected to the photo-detecting units PDU of the display area DA.

Figure 22:
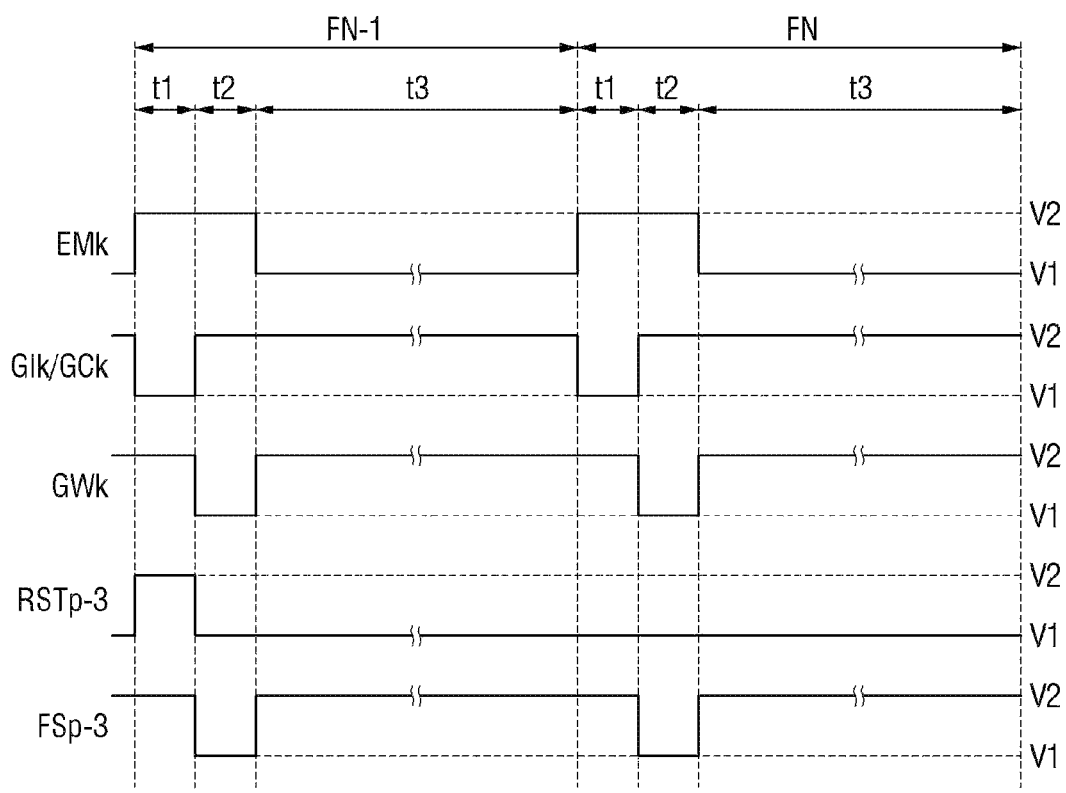
FIG. 22 is a waveform diagram showing scan signals input to the display pixel and the light-sensing pixel shown in FIG. 21 according to an embodiment of the present disclosure.

FIG. 22 is a waveform diagram showing scan signals input to the display pixel and the light-sensing pixel shown in FIG. 21 according to an embodiment of the present application.

In FIG. 22, the $k^{th}$ display emission signal Emk applied to the $k^{th}$ display emission line Elk, the $k^{th}$ display initialization signal Glk applied to the $k^{th}$ display initialization line GILk, the $k^{th}$ display control signal GCk applied to the $k^{th}$ display control line GCLk, the $k^{th}$ display scan signal GWk applied to the $k^{th}$ display write line GWLk, the $(k-3)^{th}$ reset signal RST(k-3) applied to the $(k-3)^{th}$ sense reset line RSL(k-3), and the $(k-3)^{th}$ sensing scan signal FS(k-3) applied to the $(k-3)^{th}$ light-sensing scan line FSL(k-3) during the $(n-1)^{th}$ frame period FN-1 and the nth frame period FN are shown.

The $(k-3)^{th}$ reset signal RST(k-3) applied to the $(k-3)^{th}$ sensing reset line RSL(k-3) is a signal that controls the on-off of the third sensing transistor RT3. The $(k-3)^{th}$ sensing scan signal FS(k-3) applied to the $(k-3)^{th}$ light-sensing scan line FSL(k-3) is a signal that controls the on-off of the second sensing transistor RT2.

The $(k-3)^{th}$ reset signal RST(k-3) is generated with the second level voltage V2 during the first period t1, and is generated with the first level voltage V1 during the second period t2 and the third period t3. In addition, the $(k-3)^{th}$ sensing scan signal FS(k-3) is generated with the first level voltage V1 during the first period t1 and is generated with the second level V2 during the second period t2 and the third period t3. The $(k-3)^{th}$ sensing scan signal FS(k-3) may be applied at the same timing as the $k^{th}$ display scan signal GWk.

During the first period t1, the $(k-3)^{th}$ reset signal RST(k-3) of the second level voltage V2 is supplied to the gate electrode of the third sensing transistor RT3. Accordingly, the third sensing transistor RT3 is turned on by the $(k-3)^{th}$ reset signal RST(k-3) of the second level voltage V2 to reset the second electrode of the photo-detecting element PD to the reset voltage source VRST. On the other hand, the $(k-3)^{th}$ sensing scan signal FS(k-3) having the first level voltage V1 is supplied to the gate electrode of the second sensing transistor RT2. The second sensing transistor RT2 is turned off by the $(k-3)^{th}$ sensing scan signal FS(k-3) having the first level voltage V1.

During the second period t2 and the third period t3, the $(k-3)^{th}$ reset signal RST(k-3) of the first level voltage V1 is supplied to the gate electrode of the third sensing transistor RT3. Thus, the third sensing transistor RT3 remains turned off. On the other hand, during the second period t2, the $(k-3)^{th}$ sensing scan signal FS(k-3) having the second level voltage V2 is supplied to the gate electrode of the second sensing transistor RT2. Therefore, the second sensing transistor RT2 may be turned on during the second period t2, and the first sensing transistor RT 1 may be turned off during the second period t2 and the third period t3. For example, during the third period t3, the voltage of the sensing anode electrode of the photo-detecting element PD may increase according to the light incident from the front surface.

As described above, the number of horizontal lines that allows the light-sensing pixels LSP to receive the same sensing scan signal through the respective light-sensing scan lines may be determined based on the ratio of the driving period of the light-sensing pixels LSP for each horizontal line (e.g., about 3.47 μs) to the pulse wave signal detection and conversion period of the pulse wave signal converters (e.g., about 12.8 μs). The light-sensing pixels LSP(lk-3) to LSP(lk) that receive the same sensing scan signal may output the light-sensing signals once during the pulse wave signal detection and conversion period of the pulse wave signal converters (e.g., about 12.8 μs). Accordingly, the pulse wave signal converters may stably detect the pulse wave signals using the light-sensing signals input once during the pulse wave signal detection and conversion period (e.g., about 12.8 μs).

Figure 23:
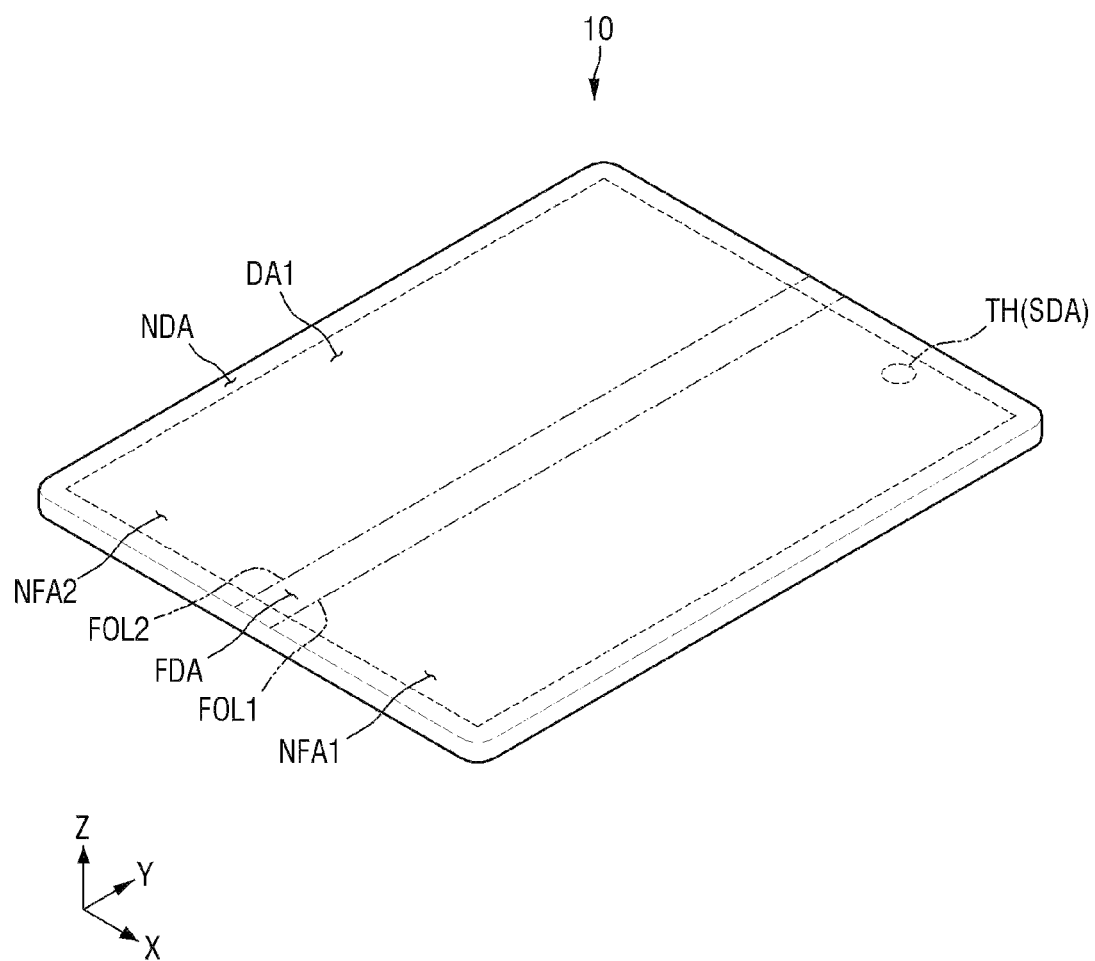
FIGS. 23 and 24 are perspective views showing a display device according to an embodiment of the present disclosure.
Figure 24:
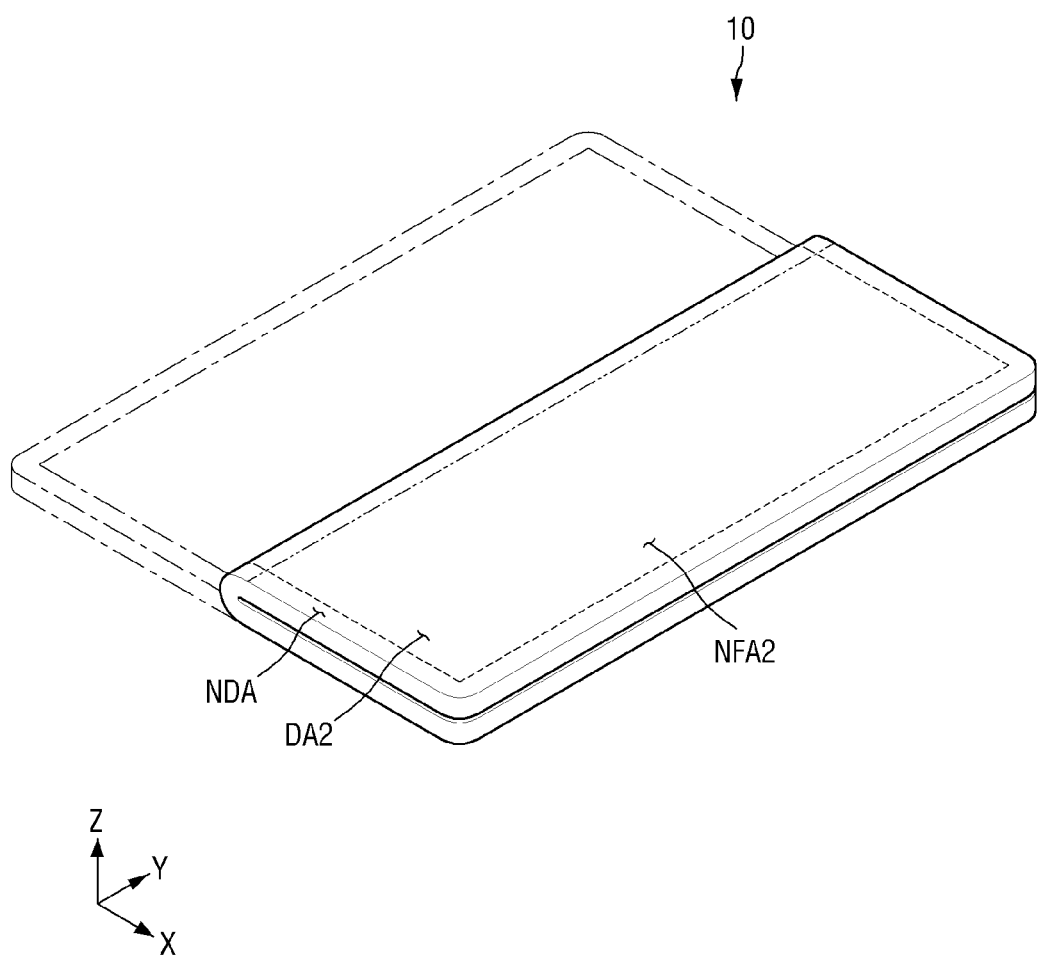

FIGS. 23 and 24 are perspective views showing a display device according to an embodiment of the present disclosure.

In the example shown in FIGS. 23 and 24, a display device 10 is a foldable display device that can be folded in the first direction (x-axis direction). The display device 10 may remain folded as well as unfolded. The display device 10 may be folded inward (in-folding manner) such that the front surface is located inside (e.g., is not visible to the user). When the display device 10 is bent or folded in the in-folding manner, a part of the front surface of the display device 10 may face the other part of the front surface. Alternatively, the display device 10 may be folded outward (out-folding manner) such that the front surface is located outside (e.g., is visible to the user). When the display device 10 is bent or folded in the out-folding manner, a part of the rear surface of the display device 10 may face the other part of the rear surface.

The first non-folding area NFA1 may be disposed on one side, for example, the right side of the folding area FDA. The second non-folding area NFA2 may be disposed on the opposite side, for example, the left side of the folding area FDA. The touch sensing unit TSU according to an embodiment of the present disclosure may be formed and disposed in each of the first non-folding area NFA1 and the second non-folding area NFA2.

The first folding line FOL1 and the second folding line FOL2 may extend in the second direction (y-axis direction), and the display device 10 may be folded in the first direction (x-axis direction). As a result, the length of the display device 10 in the first direction (the x-axis direction) may be reduced to about half, so that a user can carry the display device 10 more easily.

The direction in which the first folding line FOL1 and the second folding line FOL2 are extended is not limited to the second direction (y-axis direction). For example, the first folding line FOL1 and the second folding line FOL2 may extend in the first direction (x-axis direction), and the display device 10 may be folded in the second direction (y-axis direction) in an embodiment. In such case, the length of the display device 10 in the second direction (y-axis direction) may be reduced to about half. Alternatively, the first folding line FOL1 and the second folding line FOL2 may extend in a diagonal direction of the display device 10 between the first direction (x-axis direction) and the second direction (y-axis direction). In such a case, the display device 10 may be folded in a triangle shape.

When the first folding line FOL1 and the second folding line FOL2 extend in the second direction (y-axis direction), the length of the folding area FDA in the first direction (x-axis direction) may be smaller than the length in the second direction (y-axis direction). In addition, the length of the first non-folding area NFA1 in the first direction (x-axis direction) may be larger than the length of the folding area FDA in the first direction (x-axis direction). The length of the second non-folding area NFA2 in the first direction (x-axis direction) may be larger than the length of the folding area FDA in the first direction (x-axis direction).

The first display area DA1 may be disposed on the front side of the display device 10. The first display area DA1 may overlap the folding area FDA, the first non-folding area NFA1, and the second non-folding area NFA2. Therefore, when the display device 10 is unfolded, images may be displayed on the front side of the folding area FDA, the first non-folding area NFA1 and the second non-folding area NFA2 of the display device 10.

The second display area DA2 may be disposed on the rear side of the display device 10. The second display area DA2 may overlap the second non-folding area NFA2. Therefore, when the display device 10 is folded, images may be displayed on the front side of the second non-folding area NFA2 of the display device 10.

Although the through hole TH where a camera SDA or the like is formed is located in the first non-folding area NFA1 in FIGS. 23 and 24, the present disclosure is not limited thereto. For example, according to embodiments, the through hole TH or the camera SDA may be located in the second non-folding area NFA2 or the folding area FDA.

Figure 25:
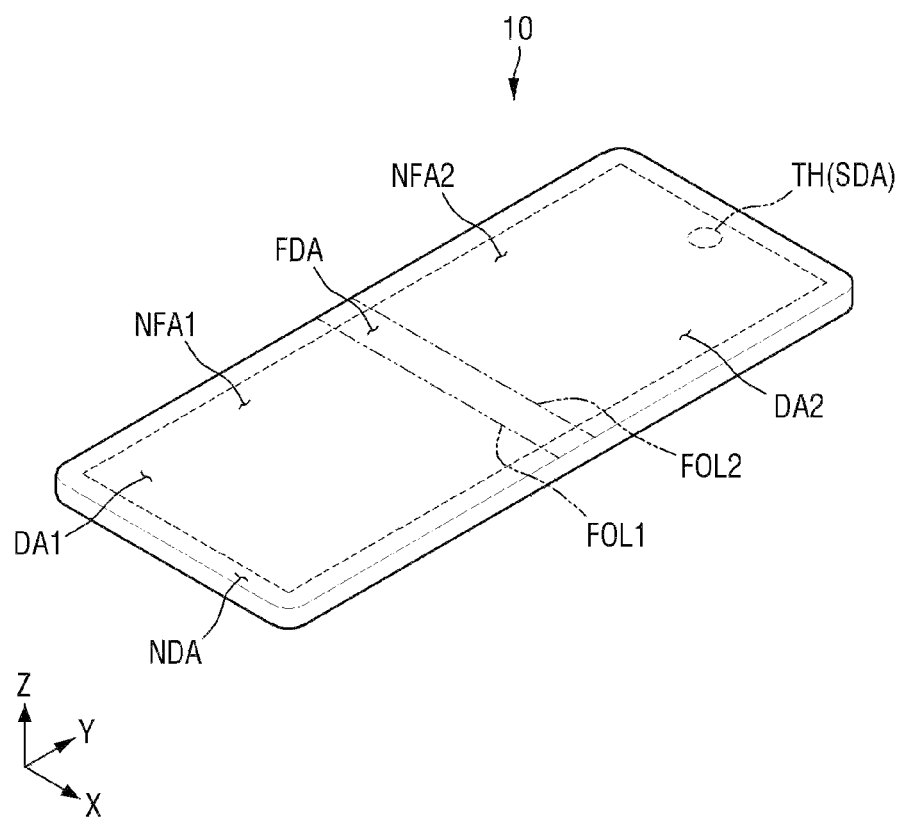
FIGS. 25 and 26 are perspective views showing a display device according to an embodiment of the present disclosure.
Figure 26:
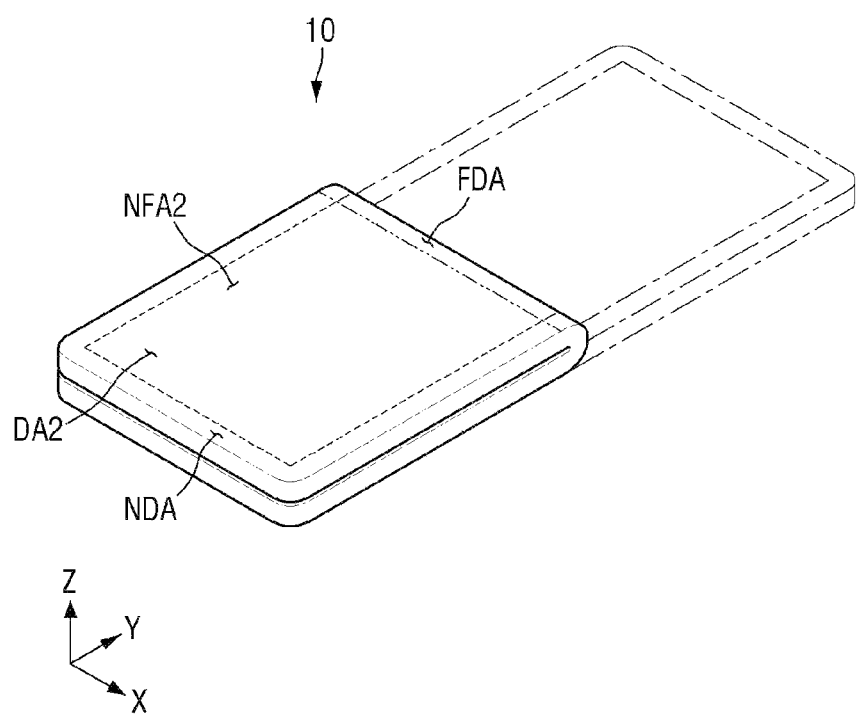

FIGS. 25 and 26 are perspective views showing a display device according to an embodiment of the present disclosure.

In the example shown in FIGS. 25 and 26, a display device 10 is a foldable display device that is folded in the second direction (y-axis direction). The display device 10 may remain folded as well as unfolded. The display device 10 may be folded inward (in-folding manner) such that the front surface is located inside (e.g., is not visible to the user). When the display device 10 is bent or folded in the in-folding manner, a part of the front surface of the display device 10 may face the other part of the front surface. Alternatively, the display device 10 may be folded outward (out-folding manner) such that the front surface is located outside (e.g., is visible to the user). When the display device 10 is bent or folded in the out-folding manner, a part of the rear surface of the display device 10 may face the other part of the rear surface.

The display device 10 may include a folding area FDA, a first non-folding area NFA1, and a second non-folding area NFA2. The display device 10 can be folded at the folding area FDA, and cannot be folded at the first non-folding area NFA1 and the second non-folding area NFA2. The first non-folding area NFA1 may be disposed on one side, for example, the lower side of the folding area FDA. The second non-folding area NFA2 may be disposed on the other side, for example, the upper side of the folding area FDA.

The touch sensing unit TSU according to an embodiment of the present disclosure may be formed and disposed on each of the first non-folding area NFA1 and the second non-folding area NFA2.

The folding area FDA may be an area bent with a predetermined curvature over the first folding line FOL1 and the second folding line FOL2. Therefore, the first folding line FOL1 may be a boundary between the folding area FDA and the first non-folding area NFA1, and the second folding line FOL2 may be a boundary between the folding area FDA and the second non-folding area NFA2.

The first folding line FOL1 and the second folding line FOL2 may extend in the first direction (x-axis direction) as shown in FIGS. 25 and 26, and the display device 10 may be folded in the second direction (y-axis direction). As a result, the length of the display device 10 in the second direction (the y-axis direction) may be reduced to about half, so that the display device 10 is easy to carry.

The direction in which the first folding line FOL1 and the second folding line FOL2 extend is not limited to the first direction (x-axis direction). For example, the first folding line FOL1 and the second folding line FOL2 may extend in the second direction (y-axis direction), and the display device 10 may be folded in the first direction (x-axis direction). In such case, the length of the display device 10 in the first direction (x-axis direction) may be reduced to about half. Alternatively, the first folding line FOL1 and the second folding line FOL2 may extend in a diagonal direction of the display device 10 between the first direction (x-axis direction) and the second direction (y-axis direction). In such a case, the display device 10 may be folded in a triangle shape.

When the first folding line FOL1 and the second folding line FOL2 extend in the first direction (x-axis direction) as shown in FIGS. 25 and 26, the length of the folding area FDA in the second direction (y-axis direction) may be smaller than the length in the first direction (x-axis direction). In addition, the length of the first non-folding area NFA1 in the second direction (y-axis direction) may be larger than the length of the folding area FDA in the second direction (y-axis direction). The length of the second non-folding area NFA2 in the second direction (y-axis direction) may be larger than the length of the folding area FDA in the second direction (y-axis direction).

The first display area DA1 may be disposed on the front side of the display device 10. The first display area DA1 may overlap the folding area FDA, the first non-folding area NFA1, and the second non-folding area NFA2. Therefore, when the display device 10 is unfolded, images may be displayed on the front side of the folding area FDA, the first non-folding area NFA1 and the second non-folding area NFA2 of the display device 10.

The second display area DA2 may be disposed on the rear side of the display device 10. The second display area DA2 may overlap the second non-folding area NFA2. Therefore, when the display device 10 is folded, images may be displayed on the front side of the second non-folding area NFA2 of the display device 10.

Although the through hole TH where the camera SDA or the like is disposed is located in the second non-folding area NFA2 in FIGS. 25 and 26, the present disclosure is not limited thereto. For example, according to embodiments, the through hole TH may be located in the first non-folding area NFA1 or the folding area FDA.

While the present disclosure has been particularly shown and described with reference to embodiments thereof, it will be understood by those of ordinary skill in the art that various changes in form and detail may be made therein without departing from the spirit and scope of the present disclosure as defined by the following claims.

What is claimed is:

1. A display device, comprising:
   a plurality of display pixels arranged in a display area of a display panel;
   a plurality of light-sensing pixels arranged alternately with the display pixels in the display area;
   a plurality of light-sensing scan lines, each divided into at least two horizontal lines disposed adjacent to each other and connected to light-sensing pixels among the light-sensing pixels disposed proximate to the at least two horizontal lines;
   a display scan driver configured to sequentially supply display scan signals to display pixels connected to each horizontal line through display scan lines corresponding to each horizontal line;
   a blood-pressure detecting circuit configured to measure a user's blood pressure using light-sensing signals input through the light-sensing pixels; and
   a display driving circuit configured to control a timing at which the display scan signals are supplied to the display scan lines and a timing at which sensing scan signals are supplied to the light-sensing scan lines.

2. The display device of claim 1, wherein the display scan driver supplies $(2i-j)^{th}$ display scan signals among the display scan signals to the light-sensing scan lines connected to the light-sensing pixels for each of the at least two horizontal lines,
   wherein the light-sensing pixels output the light-sensing signals in response to the $(2i-j)^{th}$ display scan signals, and
   wherein i is a positive integer and j is a positive integer equal to or different from i.

3. The display device of claim 2, wherein each of the display pixels comprises a light-emitting element and a pixel driving unit connected to the light-emitting element,
   wherein each of the light-sensing pixels comprises a photo-detecting element and a sensing driving unit connected to the photo-detecting element, wherein the pixel driving unit receives an $i^{th}$ display scan signal from among the display scan signals sequentially supplied through the display scan lines, and wherein the sensing driving unit receives the $(2i-j)^{th}$ display scan signals and outputs the light-sensing signals to the blood-pressure detecting circuit.

4. The display device of claim 1, wherein red, green and blue display pixels among the display pixels arranged in the display area and one light-sensing pixel among the light-sensing pixels arranged in the display area form a unit pixel, and wherein the red, green, and blue display pixels and the one light-sensing pixel are repeatedly and sequentially arranged in horizontal or vertical stripes along first and second directions of the display area.

5. The display device of claim 1, further comprising:

a light-sensing driver configured to sequentially generate the sensing scan signals for each horizontal line in response to a light-sensing control signal received from the display driving circuit, and to sequentially supply $(2i-j)^{th}$ sensing scan signals among the sensing scan signals to the light-sensing scan lines, wherein the display scan driver sequentially supplies display scan signals to the display pixels for each horizontal line in response to a write control signal from the display driving circuit, and wherein i is a positive integer and j is a positive integer equal to or different from i.

6. The display device of claim 5, wherein each of the light-sensing pixels comprises a photo-detecting element and a sensing driving unit connected to the photo-detecting element, and wherein the sensing driving unit receives the $2(i-j)^{th}$ sensing scan signals and outputs the light-sensing signals to the blood-pressure detecting circuit.

7. The display device of claim 6, further comprising:

a pressure sensing unit disposed on a front side of the display panel and configured to sense pressure applied by a user's body part and output a pressure sensing signal;

a touch sensing unit disposed on a front side of the pressure sensing unit and configured to sense a user's touch and output a touch sensing signal; and a touch driver configured to generate pressure data and pressure sensing coordinate data according to a change in a magnitude of the pressure sensing signal and a first output position, and to generate touch data and touch coordinate data according to a change in magnitude of the touch sensing signal and a second output position.

8. The display device of claim 7, wherein the display driving circuit detects and sets a touch area touched by the body part based on the touch coordinate data, arranges predetermined grayscale data for blood pressure sensing to match a position of the touch area and supplies the predetermined grayscale data to a data driver, supplies the write control signal to the display scan driver to control display pixels among the display pixels in the touch area to emit light, and supplies the light-sensing control signal to the light-sensing driver such that the $(2i-j)^{th}$ sensing scan signals are sequentially supplied to the light-sensing pixels.

9. The display device of claim 8, wherein the display driving circuit supplies coordinate information corresponding to the touch area to the blood-pressure detecting circuit, and wherein the blood-pressure detecting circuit receives the light-sensing signals through each of a plurality of sensing drivers associated with the touch area based on the coordinate information corresponding to the touch area, and detects a pulse wave signal and a blood pressure of the user.

10. The display device of claim 5, wherein the display panel further comprises a plurality of sensing reset lines, each divided into at least two additional horizontal lines disposed adjacent to each other and connected to light-sensing pixels among the light-sensing pixels disposed proximate to the at least two additional horizontal lines, and wherein the light-sensing driver sequentially generates sensing reset signals for each second horizontal line in response to the light-sensing signal received from the display driving circuit, and sequentially supplies $(2i-j)^{th}$ sensing reset signals among the sensing reset signals to the sensing reset lines.

11. The display device of claim 10, wherein each of the light-sensing pixels comprises a photo-detecting element and a sensing driving unit connected to the photo-detecting element, and wherein the light-sensing driver is reset in response to the $(2i-j)^{th}$ sensing reset signals, and outputs the light-sensing signal to the blood-pressure detecting circuit in response to the $(2i-j)^{th}$ sensing scan signals supplied after the light-sensing driver is reset.

12. The display device of claim 10, wherein each of the light-sensing scan lines and the sensing reset lines is branched into a plurality of lines and is electrically connected to the light-sensing pixels in the at least two horizontal lines.

13. The display device of claim 10, wherein the light-sensing pixels are electrically connected to one of the sensing reset lines, one of the light-sensing scan lines, and one of a plurality of sensing lines arranged in the display area, are reset by the sensing reset signals received from the sensing reset lines, and transmits the light-sensing signals to the sensing lines in response to the sensing scan signals received from the light-sensing scan lines.

14. The display device of claim 10, wherein each of the light-sensing pixels comprises a photo-detecting unit comprising a photo-detecting element, and a sensing driving unit comprising first to third sensing transistors and a sensing capacitor, and wherein the sensing capacitor is connected in parallel with the photo-detecting element.

15. The display device of claim 14, wherein the first sensing transistor allows a light-sensing current to flow to the second sensing transistor according to voltages of the photo-detecting element and the sensing capacitor, wherein the third sensing transistor supplies a reset voltage to the photo-detecting element in response to the $(2i-j)^{th}$ sensing reset signals, and wherein the second sensing transistor outputs the light-sensing signal of the photo-detecting element to a sensing line in response to the $(2i-j)^{th}$ sensing scan signals.

16. The display device of claim 15, wherein a number of horizontal lines that allow the light-sensing pixels to receive a same sensing scan signal through the respective light-sensing scan lines is determined according to a ratio of a driving period of the light-sensing pixels for each horizontal line to a pulse wave signal detection and conversion period of the blood-pressure detecting circuit.

17. The display device of claim 10, further comprising:
a pressure sensing unit disposed on a front side of the display panel and configured to sense pressure applied by a user's body part and output a pressure sensing signal;
a touch sensing unit disposed on a front side of the pressure sensing unit and configured to sense a user's touch and output a touch sensing signal; and
a touch driver configured to generate pressure data and pressure sensing coordinate data according to a change in a magnitude of the pressure sensing signal and a first output position, and to generate touch data and touch coordinate data according to a change in magnitude of the touch sensing signal and a second output position.

18. The display device of claim 17, wherein the display driving circuit detects and sets a touch area touched by the body part based on the touch coordinate data,
arranges predetermined grayscale data for blood pressure sensing to match a position of the touch area and supplies the predetermined grayscale data to the data driver,
supplies the write control signal to the display scan driver to control display pixels in the touch area to emit light, and
supplies the light-sensing control signal to the light-sensing driver such that the $(2i-j)^{th}$ sensing scan signals are sequentially supplied to the light-sensing pixels.

19. The display device of claim 18, wherein the display driving circuit supplies coordinate information corresponding to the touch area to the blood-pressure detecting circuit, and
wherein the blood-pressure detecting circuit receives the light-sensing signals through each of a plurality of sensing drivers associated with the touch area based on the coordinate information corresponding to the touch area, and detects a pulse wave signal and a blood pressure of the user.

20. The display device of claim 19, wherein a number of connections of at least two horizontal lines adjacent to each other to which the light-sensing scan lines are respectively connected is determined according to a ratio of a light-sensing driving period of the light-sensing pixels for each horizontal line to a pulse wave signal detection period of the blood-pressure detecting circuit.

\* \* \* \* \*